United States Patent
Suzuki et al.

(10) Patent No.: US 9,878,174 B2
(45) Date of Patent: Jan. 30, 2018

(54) HIGH FREQUENCY CANCER THERMOTHERAPY APPARATUS

(71) Applicant: SHONAI CREATE INDUSTRIAL CO., LTD., Yamagata (JP)

(72) Inventors: Masanori Suzuki, Yamagata (JP); Hiroaki Ikehara, Yamagata (JP)

(73) Assignee: SHONAI CREATE INDUSTRIAL CO., LTD., Yamagata (JP)

(*) Notice: Subject to any disclaimer, the term of this patent is extended or adjusted under 35 U.S.C. 154(b) by 0 days.

(21) Appl. No.: 15/038,246

(22) PCT Filed: Nov. 14, 2014

(86) PCT No.: PCT/JP2014/080170
§ 371 (c)(1),
(2) Date: May 20, 2016

(87) PCT Pub. No.: WO2015/079931
PCT Pub. Date: Jun. 4, 2015

(65) Prior Publication Data
US 2016/0287891 A1    Oct. 6, 2016

(30) Foreign Application Priority Data
Nov. 26, 2013    (JP) ................. 2013-243437

(51) Int. Cl.
*A61N 1/40* (2006.01)
*A61N 1/04* (2006.01)
*A61N 1/06* (2006.01)

(52) U.S. Cl.
CPC .......... *A61N 1/403* (2013.01); *A61N 1/0492* (2013.01); *A61N 1/06* (2013.01)

(58) Field of Classification Search
CPC combination set(s) only.
See application file for complete search history.

(56) References Cited

U.S. PATENT DOCUMENTS

| 5,046,495 A * | 9/1991 | Takahashi ............... A61N 1/403 5/613 |
| 2008/0009696 A1 * | 1/2008 | Hempel ................. A61B 5/055 600/407 |
| 2012/0023671 A1 * | 2/2012 | Miyano ................ A61B 6/0407 5/601 |

FOREIGN PATENT DOCUMENTS

| JP | 63-145671 | 6/1988 |
| JP | 63-145672 | 6/1988 |

(Continued)

OTHER PUBLICATIONS

International Search Report dated Feb. 24, 2015 in International (PCT) Application No. PCT/JP2014/080170.

(Continued)

*Primary Examiner* — Joseph Stoklosa
*Assistant Examiner* — Adam Avigan
(74) *Attorney, Agent, or Firm* — Wenderoth, Lind & Ponack, L.L.P.

(57) ABSTRACT

A high frequency cancer thermotherapy apparatus treats by generating a high frequency electric field between a pair of electrode parts which sandwich a patient and are disposed so as to be opposite to each other and perform a dielectric heating with respect to an affected part. The apparatus includes a bed having a bed part and a bed supporting part for liftably/lowerably and horizontally movably supporting the bed part, a gantry on which the electrode parts are mounted, and a high frequency generation and control part. A maximum-sized electrode part which can be mounted on the gantry includes an electrode plate having a diameter exceeding 300 mm and a pad attached on the electrode plate. The bed part includes an opening part formed such that the maximum-sized electrode part can pass from a vertical direction, a shutter which opens/closes the opening part, and a bed surface flatization device.

5 Claims, 9 Drawing Sheets

(56) References Cited

FOREIGN PATENT DOCUMENTS

| | | |
|---|---|---|
| JP | 7-8564 | 1/1995 |
| JP | 7-108066 | 4/1995 |
| JP | 10-24112 | 1/1998 |
| JP | 2000-210300 | 8/2000 |
| JP | 2003-169855 | 6/2003 |
| JP | 2005-131033 | 5/2005 |
| JP | 2012-223339 | 11/2012 |
| JP | 2013-106676 | 6/2013 |
| WO | 2013/002498 | 1/2013 |

OTHER PUBLICATIONS

Written Opinion of the International Searching Authority dated Feb. 24, 2015 in International (PCT) Application No. PCT/JP2014/080170 with English Translation.

"A High Frequency Type Hyperthermia System Thermotron (Registered Trademark)—RF8", "Online", Pharmaceuticals and Medical Devices Agency, Pharmaceuticals and Medical Devices Information Providing Homepage (Information About Attached Documents of Medical Devices), "Searching That Was Carried Out on Jul. 5, 2013", Internet "URL:http://www.info.pmda.go.jp/ygo/pack/15900BZZ01728000_A_01_01/15900BZZ01728000_A_01_01?view=body".

"Thermotherapy of Cancers: Information About Hyperthermia", "Online", Social Healthcare Corporation Tei-Shin-Kai Shinsapporo Keiaikai Hospital, "Searching That Was Carried Out on Jul. 5, 2013", Internet "http://www.teishinkai.jp/skhp/hyperthermia.html".

Extended European Search Report dated Jul. 25, 2017 in European Application No. 14865325.6.

\* cited by examiner

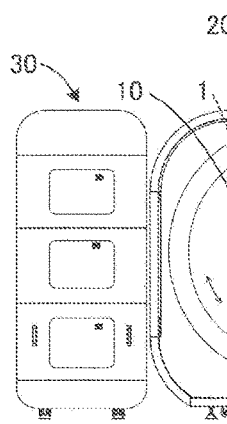
FIG.1A
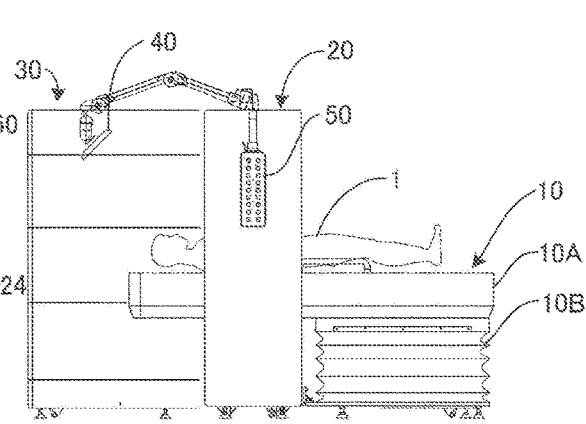
FIG.1B
FIG.2
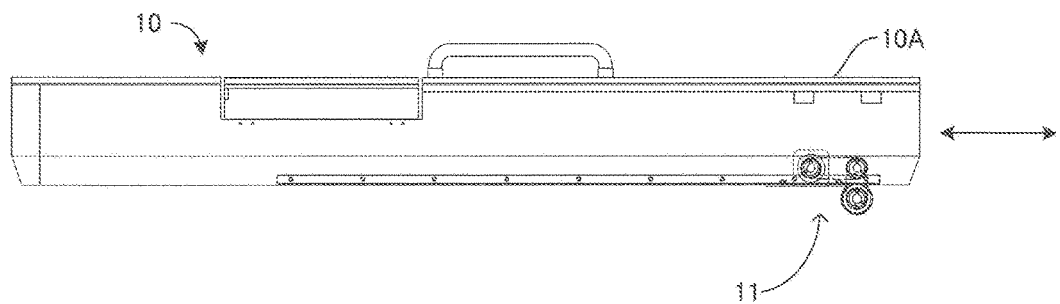

STATE THAT SHUTTER IS CLOSED

A-ARROW VIEW

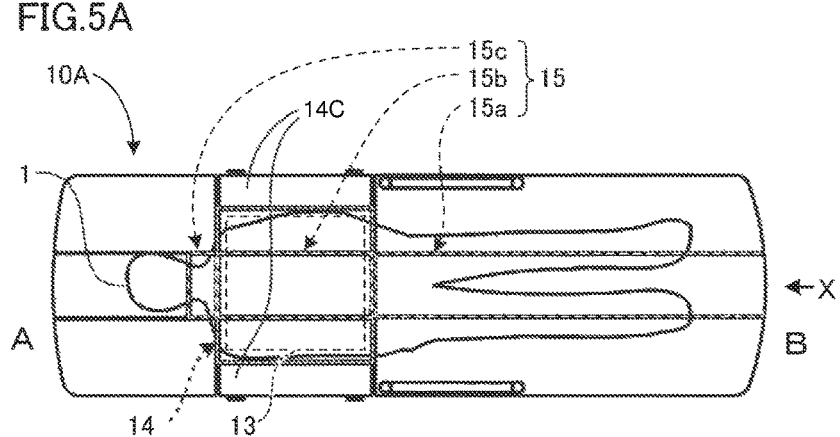
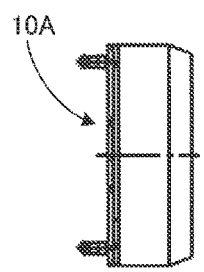
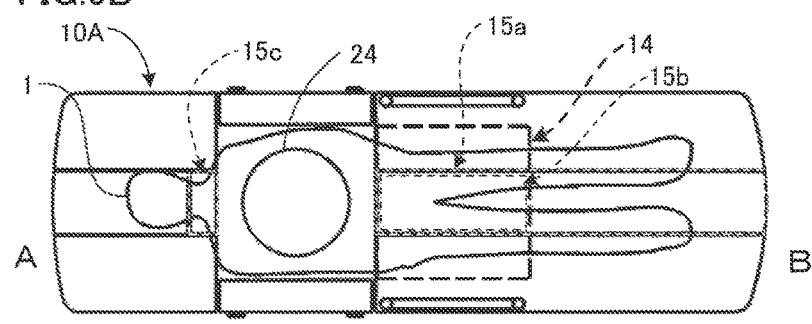

HIGH FREQUENCY CANCER THERMOTHERAPY APPARATUS

TECHNICAL FIELD

The present invention relates to a treatment apparatus for an affected part of a human body by means of thermotherapy (hereinafter, also referred to as "hyperthermia"), and in particular to an improved technique of a high frequency cancer thermotherapy apparatus (hereinafter, also referred to as "a high frequency thermotherapy system" or "a high frequency hyperthermia system") that treats by generating a high frequency electric field between a pair of electrodes which sandwich a patient and are disposed so as to be opposite to each other and performing a dielectric heating with respect to an affected part of the patient.

BACKGROUND ART

Conventionally, a technique that treats by performing the dielectric heating with respect to the affected part by means of the high frequency electric field generated between electrodes is known.

Although an apparatus which is called Thermotron (registered trademark)-RF8 and is manufactured by YAMAMOTO VINITA CO., LTD. is well known as a high frequency cancer thermotherapy apparatus using this technique (hereinafter, simply referred to as "a thermotherapy apparatus"), this thermotherapy apparatus was developed 30 years ago and is being used so far with hardly being improved.

Although the above Thermotron (registered trademark)-RF8 is an apparatus developed from a viewpoint of symptomatic therapy as a prognosis treatment apparatus of radiation treatment, recently, attentions are focused on a fact that as a matter of fact, a technique of necrotizing cancer cells by utilizing the principle of the dielectric heating using high frequency and heating the cancer cells up to 42.5° C. or higher has an effect of improving immune functions of normal cells, and the above matter draws attention as a therapeutic method that can change current cancer treatment.

Concretely, in the high frequency thermotherapy apparatus, although the cancer cells are necrotized by heating the cancer cells up to 42.5 degrees Celsius or higher (for example, around 45° C.), since a body temperature which is lower than the cancer cells is maintained according to a cooling action caused by blood circulation when the normal cells are heated, a fact is that surrounding normal cells are heated up to around 40° C. at the same time, attentions are focused on a fact that the above fact has an effect of improving the immune functions of the normal cells, regulating a microenvironment, preventing and/or reducing spreading of the cancer, and changing the surfaces of the cancer cells to a condition which raises the effect of drugs, and this matter draws attention as the therapeutic method that can change the current cancer treatment that depends only on three major symptomatic therapies which are called operative therapy, chemotherapy (anticancer agents) and radiotherapy.

Here, the configuration of a conventional thermotherapy apparatus will be described with reference to FIG. 12.

FIG. 12 is an appearance diagram showing one example of the conventional thermotherapy apparatus and shows the configuration of an ultrashort-wave warming therapeutic apparatus disclosed in Patent Document 2. This ultrashort-wave warming therapeutic apparatus comprises a therapy table part 51 on which a patient as a subject to be treated lies down, a gantry 52 for irradiating the inside of a living body with a high frequency, a high frequency generation part 53 for generating the high frequency of a MHz band (for example, 8 MHz), and a control part 54 for controlling the driving of the ultrashort-wave warming therapeutic apparatus itself.

As shown in the example of FIG. 12, a main body central part of the gantry 52 is provided with a through hole 501, and an inside surface of the through hole 501 is provided with a supporting part 502 which is rotatable with respect to a gantry main body. Further, the supporting part 502 is protrusively provided with arms 506 and 507 which are expansible/contractible in a diameter direction, and the tips of the arms 506 and 507 are provided with disk-shaped electrode plate 508 and 509.

Electrode parts 504 and 505 comprise the above arms 506 and 507, the above electrode plate 508 and 509, and cooling pads 510 and 511 which are attached on the surfaces of the electrode plates 508 and 509 (the surfaces spliced on the living body). When performing treatment, the arms 506 and 507 of the electrode parts 504 and 505 are expanded/contracted so as to splice the electrode plate 508 and 509 on the patient.

The above cooling pads 510 and 511 are a cooling means which suppresses heating on the surface of the living body in the vicinity of the electrodes in the case that the affected part exists in a deep layer region of the living body, it is configured to circulate cooling water within the cooling pads 510 and 511, and it is possible to suppress the heating on the surface of the living body and relieve thermal pains inflicted on the patient under treatment by means of the cooling pads 510 and 511 (the above, refer to Patent Document 2).

Further, as an apparatus for ensuring maintenance support of a body position under treatment, for example, there is a conventional invention disclosed in Patent Document 3. The conventional invention disclosed in Patent Document 3 comprises an air mattress comprised of an assembly comprising a plurality of cells filled with air and a turnable backrest part so as to ensure the maintenance support of the body position of the patient while keeping various body positions. For example, in the case of performing treatment in a recumbent position, air is sent only to cells on one side of a width direction (or air is let out) so as to help a laterally facing treatment, and in the case that the affected part is an abdomen or the like, the backrest part is lifted only a predetermined angle so as to become a somewhat-get-up position. In addition, the conventional invention disclosed in Patent Document 3 has one aspect that employs a separately-excited oscillation method based on a first frequency and a second frequency and irradiates the affected part with a high frequency electric field of a high frequency corresponding to the depth of the affected part so as to eliminate the need for an electrode exchanging work performed in the conventional thermotherapy apparatus, for example, an exchanging work that temporarily interrupts operations in the middle of warming in the case that the affected part exists in both a surface layer and a deep region and then changes a combination of electrodes.

However, although the conventional invention disclosed in Patent Document 3 has one aspect of eliminating the need for the electrode exchanging work as described above, a pair of electrodes 508 and 509 exemplified in FIG. 12 generally uses electrodes which have different electrode sizes in accordance with the depth of the affected part to be treated. For example, in Thermotron (registered trademark)-RF8 which is manufactured by YAMAMOTO VINITA CO., LTD. in Japan, electrodes used for treatment have six kinds of electrodes whose diameter φ is 70 mm, 100 mm, 140 mm, 210 mm, 250 mm and 300 mm. Further, a lesioned part is treated in accordance with a combination of electrodes suitable for a part to be warmed, concretely, in the case of warming of a superficial lesioned part (superficial focus), the electrode of 70 mm or 100 mm in diameter and the electrode of 250 mm or 300 mm in diameter are used after making them to become opposed to each other, in the case of warming of a latent lesioned part (latent focus), the electrode of 140 mm in diameter and the electrode of 250 mm or 300 mm in diameter are used after making them to become opposed to each other, and in the case of warming of a deep-seated lesioned part, the electrode of 210 mm in diameter and the electrode of 250 mm or 300 mm in diameter are used after making them to become opposed to each other (refer to descriptions of "attentions relating to treatment" in Non-Patent Document 1).

Further, the therapy table part 51 exemplified in FIG. 12 can be adjusted in a range of its height approximately from 740 mm to 900 mm (in Non-Patent Document 1, from 770 mm to about 980 mm) by a lifting/lowering mechanism, and a predetermined position of the therapy table is provided with an opening part for lower electrode pass. Furthermore, during performing treatment in a supine position or a prone position, the procedure is that after performing setting of the opening part of the therapy table part, the patient is put on the therapy table, and then, after moving the therapy table to the through hole of the gantry and setting the electrodes, warming therapy is started (refer to descriptions of "dimension and weight of each part", "selection and combination of electrodes", etc. in Non-Patent Document 1).

In the treatment using the high frequency thermotherapy apparatus described as above, although the number of treatments and a treatment time are different depending on disease, for example, the treatment time (a warming time) of one time of treatment is about 40 minutes, and 5 to 10 times of treatment are performed at apace of 1 to 2 times per week (for example, refer to Non-Patent Document 2).

THE LIST OF PRIOR ART DOCUMENTS

Patent Documents

Patent Document 1: Japanese Published Unexamined Patent Application No. H7-85664 A
Patent Document 2: Japanese Published Unexamined Patent Application No. H10-24112 A
Patent Document 3: Japanese Published Unexamined Patent Application No. 2012-223339 A Non-Patent Documents Non-Patent Document 1: "a high frequency type hyperthermia system Thermotron (registered trademark)-RF8", "online", Pharmaceuticals and Medical Devices Agency, Pharmaceuticals and Medical Devices information providing homepage (information about attached documents of Medical Devices), "searching that was carried out on Jul. 5, 2013", Internet "URL:http://www.info.pmda.go.jp/ygo/pack/15900BZZ0172 8000_A_01_01/15900BZZ01728000_A_01_01?view=body"
Non-Patent Document 2: "thermotherapy of cancers: information about hyperthermia", "online", social healthcare corporation tei-shin-kai Shinsapporo Keiaikai Hospital, "searching that was carried out on Jul. 5, 2013", Internet "http://www.teishinkai.jp/skhp/hyperthermia.html"

Problems to be Solved by the Invention

As mentioned above, the technique of treating cancers by utilizing the principle of the dielectric heating using a high frequency has the effect of concurrently boosting immunity of the surrounding normal cells.

However, in the conventional thermotherapy apparatus, even in the case of the maximum electrode, its size (the diameter φ) is 300 mm (refer to Non-Patent Document 1), a range that the normal cells are heated up to around 40° C. (a temperature that improves the immune functions) is narrower than electrode size, and in order to further boost the immunity of the normal cells, it is desired to perform heating of a wider range.

However, in order to make an electrode having a diameter size of approximately a horizontal width of a human body of a common adult (for example, about 400 mm) available, in the conventional thermotherapy apparatus, it is necessary to solve the following problems. Further, "the conventional thermotherapy apparatus" referred to here means an apparatus manufactured by YAMAMOTO VINITA CO., LTD. (Thermotron (registered trademark)-RF8).

(1) Interference of the Electrodes with the Therapy Table

In the conventional thermotherapy apparatus, the sizes of the opening part of the therapy table (and a shutter which blocks the opening part in the laterally facing treatment) are molded in accordance with 300 mm being the maximum diameter size of the electrode. As a result, even if a large-sized electrode having a size that the diameter φ exceeds 300 mm (for example, the electrode having the diameter size of approximately the horizontal width of the human body of the common adult) is developed, in the case of treatment based on a high frequency electric field from up and down directions, since a lower electrode interferes with the opening part of the therapy table, it is impossible to apply the large-sized electrode. Further, in the case of treatment based on a high frequency electric field from a lateral direction, since a pad part of the large-sized electrode interferes with parts of both sides (upper parts of side parts) in a width direction of the therapy table, there is a problem that it is impossible to apply the large-sized electrode.

(2) Reduction of Adhesiveness of an Electrode Surface to a Body Surface of the Patient The conventional thermotherapy apparatus change angles of the electrode plate 508 and 509 by rotating the supporting part 502 of the electrodes exemplified in FIG. 12 with respect to the main body of the gantry 52. In this case, the surfaces of the electrode plate 508 and 509 become a movement along an inside surface of the gantry main body (an arc-shaped movement which is centered on a center part of a circular opening part of the gantry main body). As a result, in the conventional thermotherapy apparatus, when the diameter size of the electrode plate is enlarged to the size of approximately the horizontal width of the human body of the common adult, it is considered that the adhesiveness to the body surface of the patient gets worse and an incident quantity of an electric force line into patient's body decreases.

(3) Problems Relating to a Mattress

Although it is necessary to enlarge the size of the therapy table and the size of the mattress which is spread out on the therapy table during the treatment in the recumbent position with the enlargement of the electrode size, a problem of an installation space occurs. Here, a mattress used in a general high frequency thermotherapy apparatus during the treatment in the recumbent position will be described.

The conventional thermotherapy apparatus can perform the treatment based on the high frequency electric field from the lateral direction (the treatment in the recumbent position) by rotating the supporting part 502 of the electrodes exemplified in FIG. 12 by 90 degrees from the up and down directions (a vertical direction) to the lateral direction (a horizontal direction) by using a rotating drum which is rotatable steplessly. However, since the shutter which blocks the opening part of the therapy table is located below an upper surface of the therapy table, a level difference occurs between a shutter part and other part except that, and there is a possibility of getting injured due to the level difference. Further, since the therapy table has toughness, there is a problem that it is difficult for the patient to keep the recumbent position over a long time. Hence, conventionally, when performing the treatment based on the high frequency electric field from the lateral direction, a therapist (a doctor) deals with the above problem by using one aspect of spreading the mattress out on the therapy table that the opening part is blocked by the shutter and putting the patient on the mattress. Further, in the treatment based on the high frequency electric field from the lateral direction, in the case of for example using the electrode that the diameter $\varphi$ is 300 mm without using the large-sized electrode described above, since a pad part of an electrode lower part interferes with the upper parts of the side parts of the therapy table, conventionally, the above interference is avoided by forming a convex mattress by spreading a longitudinal mattress having a width shorter than a width of the therapy table out again on the above mattress, making a central part in a longitudinal direction of the therapy table higher by doing so, and disposing the electrode part in both side parts (low parts) of the convex mattress.

Hence, since it is necessary for the conventional thermotherapy apparatus to ensure a mattress storage space in a treatment room, there is the problem of the installation space. Further, since there are a mattress laying work and a mattress removing work, there is also a problem that burdens on the doctor are also heavy.

(4) Leakage of Electromagnetic Waves

In the conventional thermotherapy apparatus, since the length of the depth of the gantry part is also molded in accordance with 300 mm being the maximum diameter size of the electrode, in the case of employing the large-sized electrode, a portion of the electrode protrudes in a depth direction of the gantry part and the electromagnetic waves leak to outside.

In the case of enlarging the size of the therapy table and the size of the mattress which is spread out on the therapy table with the enlargement of the electrode size, there is a possibility that these problems are further in question.

(5) Problems Relating to Reducing of Burdens on the Patient

As described above, in order to enlarge the electrode size and improve therapeutic effects, although it is necessary to improve the conventional thermotherapy apparatus, it is desired to perform remodeling that reduces the burdens on the patient along with the improvement.

As the problems relating to reducing of the burdens on the patient, there are the following problems.

As the first problem, although the conventional thermotherapy apparatus comprises a display part for monitoring warming conditions, patient's therapeutic situation etc., this display is provided for doctor, and the patient himself/herself cannot visually confirm the therapeutic situation etc. during treatment and has to stay motionless for a long time without understanding the situation.

Hence, it is considered that patient's anxiety feeling is significant in comparison with a common treatment such as the radiation treatment which finishes in a relatively short time. In particular, when the diameter size of the electrode plate is enlarged, since an apparent oppressive feeling increases in comparison with a conventional electrode size, there is a possibility that the patient's anxiety feeling increases.

As the second problem, in the conventional thermotherapy apparatus, when performing the treatment, the temperature of the affected part is directly measured by pricking with a needle-like temperature sensor or the temperature of the affected part within a cavity is measured from the patient's mouth by inserting a temperature sensor into the cavity each time, a supply of high frequency energy is controlled based on a temperature measurement value so that a rise temperature of cancer cells becomes (enters) a predetermined temperature range, and pains due to inserting of the temperature sensor are given to the patient. Further, since the high frequency of the apparatus has an influence on the temperature sensor, a large error occurs in the affected part's temperature measurement.

As the third problem, since the conventional thermotherapy apparatus pushes lifting/lowering of the therapy table part up to a center position of the gantry part (to 900 mm) by a hydraulic cylinder, a height during lowering (the lowest height of the therapy table part) can only lower to about a value 740 mm obtained by totaling "a height of casters", "a length of the cylinder" and "a pushing mechanism (a thickness of the therapy table part)" (in Non-Patent Document 1, the above value is 770 mm). Hence, even in the case of maximally lowering, patient's getting in/out of the therapy table is not easy.

As the fourth problem, when the conventional thermotherapy apparatus performs a temperature control of cold water within the pads of the electrode part, even though surface and reverse temperatures of the body surface of the patient are different, since the temperature control is performed concurrently with respect to a pair of pads (two pads), it is difficult to control at an optimum temperature to aim for, as a result, it is hard to realize a temperature setting that is the most desirable for the patient.

As the fifth problem, in order to increase a degree of adhesion to the patient of the electrode pad, although the pads are pressed to the patient, there is no control of a pressing force (alarm), and a measure against applying an abnormal pressure to the patient is not carried out.

As the sixth problem, feedback from the patient after treatment, therapeutic effects, etc. are not associated with treatment execution records to record. As a result, it is not easy to manage evidences for treatment.

SUMMARY OF THE INVENTION

The present invention has been developed in view of the above-described problems, and the object of the present invention is to provide a high frequency cancer thermotherapy apparatus capable of improving the therapeutic effects and reducing the burdens on the patient.

Means for Solving the Problems

The present invention relates to a high frequency cancer thermotherapy apparatus that treats by generating a high frequency electric field between a pair of electrode parts which sandwich a patient and are disposed so as to be opposite to each other and performing a dielectric heating with respect to an affected part of said patient, the above-described object of the present invention is achieved by that comprising: a bed for thermotherapy that comprises a bed part on which said patient lies down and a bed supporting part for liftably/lowerably and horizontally movably supporting said bed part; a gantry that comprises a pair of expanding/contracting arms which are disposed so as to protrude from an inner peripheral surface of a rotating ring (also referred to as "a rotating drum") which can control so as to pivot around said bed part and be opposite to each other, and on which said electrode parts are mounted; and a high frequency generation and control part that generates said high frequency electric field and performs a control with respect to each part of said high frequency cancer thermotherapy apparatus, wherein a maximum-sized electrode part which can be mounted on said gantry is an electrode part comprising an electrode plate having a size that a diameter size exceeds 300 mm and a pad attached on said electrode plate, wherein said bed part comprises an opening part which is formed to a size that said maximum-sized electrode part can pass from a vertical direction; a shutter which opens/closes said opening part; and a bed surface flatization means which comprises slide type tables for flatizing a level difference in a bed surface of said bed part which occurs in a state of closing said opening part by said shutter.

Further, the above-described object of the present invention is more effectively achieved by that wherein said maximum-sized electrode part is configured to comprise an electrode plate having a diameter size at the same level as a horizontal width of a human body of an average adult; or wherein comprising an electrode pad tightly-adhering means for making a surface of said electrode part adhere tightly to a body surface of said patient, and wherein said electrode pad tightly-adhering means comprises a spherical joint which tiltably supports said electrode part provided on a tip part of said expanding/contracting arm in an arbitrary direction; an electrode angle fixing means which fixes a tilting angle of said electrode part; and a pad surface which is made of a soft material; or wherein comprising a display for patient which is provided at a position where said patient on said bed for thermotherapy under treatment can view; and a display control means which displays information showing said patient's therapeutic situation under treatment based on said dielectric heating or videos and audios for appreciation purpose in said display for patient; or wherein said bed supporting part comprises a bed part lifting/lowering means capable of lowering until a height from a floor surface that said bed for thermotherapy is installed on to an upper surface of said bed part becomes about 500 mm; or wherein said bed part lifting/lowering means is comprised of a pantographic arm type lifting/lowering device; or wherein a means for horizontally moving said bed part is configured to comprise a servomotor and its drive control means; or wherein said slide type tables comprise a first division table that a length in a longitudinal direction of said bed part is longer than a length of said shutter and a second division table that said length in said longitudinal direction of said bed part is the same as said length of said shutter, and are configured that in a case of a first treatment aspect that treats by means of a vertical direction's high frequency from said electrode parts, said second division table is united with said shutter and housed in a lower part of said bed part in a state that said patient lies down on said bed part, in a case of a second treatment aspect that treats by means of a horizontal direction's high frequency from said electrode parts, said first division table is installed across both sides of said opening part in said longitudinal direction of said bed part, and concurrently, interference of a part of a pad of said electrode part with parts of both sides in a width direction of said bed part is avoided by lowering said shutter which closes said opening part by a predetermined distance; or wherein a pad of said electrode part is a pad capable of switching cold water and warm water that flow within said pad and comprises a temperature adjusting means which adjusts a temperature of said pad of said electrode part for every said pad by separately performing temperature control of said cold water and said warm water for every said pad of said pair of electrode parts; a means which monitors flow rates of said cold water and said warm water; and a means which monitors abnormality in a pressing force of said pad against a body surface of said patient; or wherein said temperature adjusting means preliminarily warms a temperature of said pad by said warm water before bringing said pad into contact with said body surface of said patient so that said temperature of said pad becomes within a normal body temperature range of said patient's body temperature, and switches from said warm water to said cold water so as to lower said temperature of said pad in accordance with operations after bringing said pad into contact with said body surface of said patient; or wherein said high frequency generation and control part controls a supply of high frequency energy to said electrode plate based on a measured temperature having a small error obtained by removing noise of detection data of a temperature sensor for detecting a temperature of said affected part during a first treatment of said patient so that said temperature of said affected part becomes a predetermined temperature range and concurrently records measurement data of a living body impedance of said patient, and comprises a heating control means which controls a supply of high frequency energy to said electrode plate based on record data of said living body impedance of said patient without using said temperature sensor during treatment of said patient from a second time so that said temperature of said affected part becomes said predetermined temperature range; or wherein said gantry is formed so that a width in a depth direction of said rotating ring is a length which exceeds a diameter size of said maximum-sized electrode part and a shielding plate made of aluminum is stuck on an inner face of an exterior of said gantry's frame; or wherein a diameter size of an electrode plate of said maximum-sized electrode part is within a range of 350 mm to 500 mm; or wherein a diameter size of an electrode plate of said maximum-sized electrode part is 400 mm; or wherein said high frequency cancer thermotherapy apparatus is connected to a computer for doctor via a communication means, wherein said computer for doctor comprises a patient data recording means which associates said patient's patient information, said patient's diagnosis information, various kinds of measurement data during treatment based on said dielectric heating and said patient's QOL survey results with each said patient and records them as patient data; and a patient data browsing means which displays said patient data in a display device in accordance with a browsing operation performed by said computer for doctor.

Effects of the Invention

According to the present invention, since it becomes possible to perform treatment by using electrodes having an electrode plate having a size that a diameter size exceeds 300 mm (for example, an electrode plate having the diameter size at the same level as a horizontal width of a human body of an average adult), in comparison with a conventional apparatus, it becomes possible to necrotize cancer stem cells having a possibility of attracting extensive metastases by further improving the immunity of a wide range of normal cells on the periphery of the affected part. Further, since the mattress which is laid on the upper surface of the therapy table part by the doctor and the mattress storage space becomes unnecessary, and carrying around of the mattress and the mattress laying work also become unnecessary, the burdens on the doctor are reduced, concurrently, it becomes possible to use the space used for the mattress storage space for other purposes.

Moreover, by employing a configuration of comprising an electrode pad tightly-adhering means, more stable and more electric force line can be made incident into the patient's body, and concurrently it becomes possible to improve an uncertain tightly-adhering state between the electrode and the body surface of the patient.

Further, by employing a configuration of comprising a display for patient, it becomes possible to visually confirm the therapeutic situation of the patient himself/herself during treatment, in comparison with the conventional apparatus, it is possible to reduce anxious thoughts caused by a matter that the patient does not understand the therapeutic situation at all and mental burdens on the patient during treatment by viewing videos for appreciation purpose or listening to audios for appreciation purpose.

Further, by employing a configuration of comprising abed part lifting/lowering means capable of lowering until becoming about 500 mm, in comparison with the conventional apparatus, it becomes possible to reduce physical burdens of the patient's getting in/out of the therapy table.

Further, by employing a configuration of comprising a temperature adjusting means of pads, it becomes possible to relieve pains caused by coldness that the patient felt when bringing the pads into contact with the body surface of the patient (coldness of the cooling pads of the conventional apparatus) and the thermal pains during thermotherapy.

Further, by reducing the influence of the high frequency of the apparatus, in comparison with a conventional measured temperature having a large measurement error (for example, the measurement error is about 1 degree Celsius), the measurement error can be reduced to about half of the conventional one (for example, the measurement error is 0.5 degree Celsius) or less.

Further, by employing a configuration of comprising a heating control means based on record data about a living body impedance, with respect to a patient having one time of treatment result, it becomes possible to avoid the patient's pains due to inserting of the temperature sensor during treatment from the second time.

Further, by employing a configuration that a gantry is formed so that a width in a depth direction is a length which exceeds a diameter size of a maximum-sized electrode part and concurrently a shielding plate made of aluminum is stuck on an inner face of an exterior of the gantry's frame, even in the case of using a large-sized electrode that the diameter size exceeds 300 mm, it is possible to inhibit the leakage of the electromagnetic waves to outside.

BRIEF DESCRIPTION OF THE DRAWINGS

In the accompanying drawings:

FIGS. 1A and 1B are diagrams schematically showing one example of an overview configuration of a high frequency cancer thermotherapy apparatus according to the present invention;

FIG. 2 is a cross-section diagram schematically showing an internal structure of a bed part according to the present invention;

FIGS. 5A, 5B and 5C are diagrams for explaining a bed surface flatization means according to the present invention;

MODE FOR CARRYING OUT THE INVENTION

Figure 3:
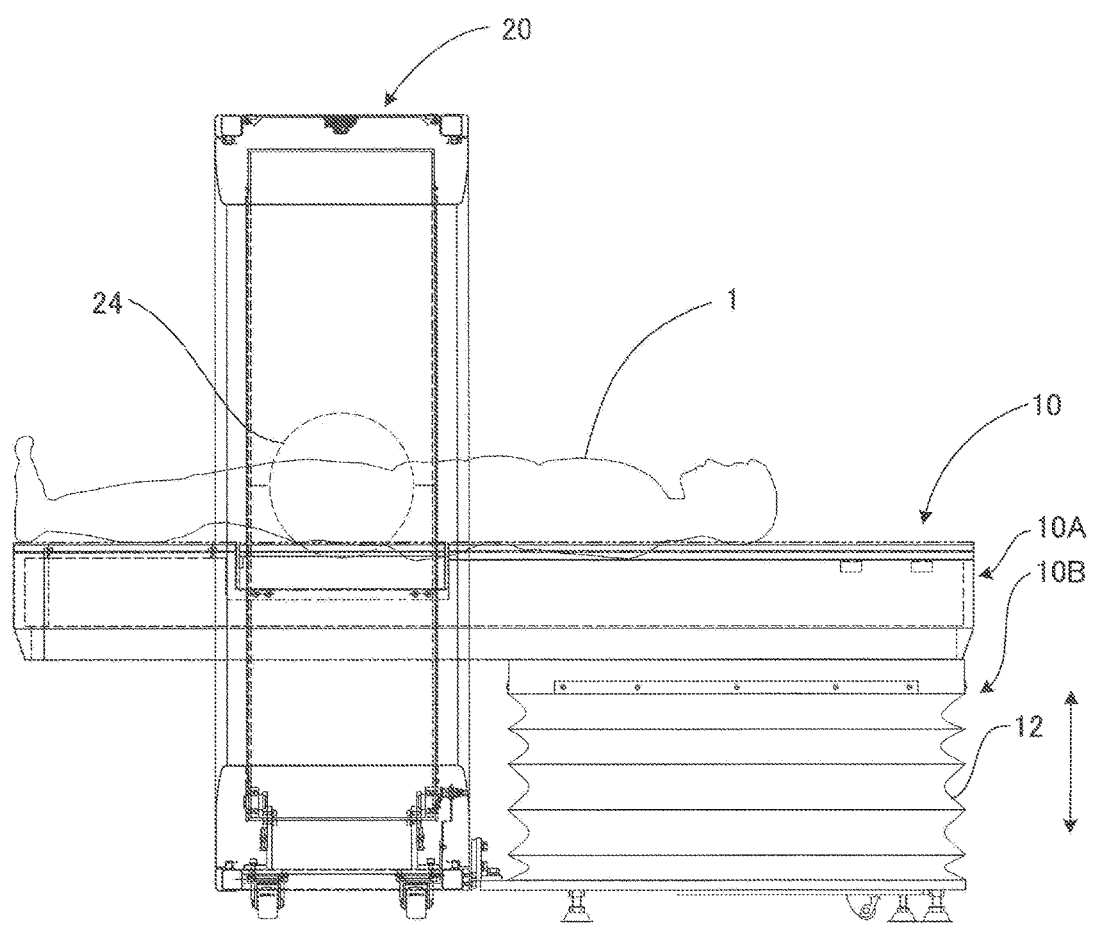
FIG. 3 is a cross-section diagram schematically showing a configuration of a bed supporting part according to the present invention.

Hereinafter, preferred embodiments of the present invention will be described with reference to the accompanying drawings.

FIGS. 1A and 1B are schematic diagrams showing one example of an overview configuration of a high frequency cancer thermotherapy apparatus according to the present invention (hereinafter, simply referred to as "a thermotherapy apparatus"), FIG. 1A is a front view and FIG. 1B is a side view.

In FIGS. 1A and 1B, as a main configuration, the thermotherapy apparatus is configured by comprising a bed for thermotherapy 10 where a patient 1 as a subject to be treated gets in, a gantry 20 for performing a dielectric heating with respect to an affected part (and its peripheral part) of the patient 1 on the bed by irradiating with a high frequency from electrode parts 24 (24A, 24B), a high frequency generation and control part 30 for generating a high frequency electric field and performing an action control with respect to each part of the thermotherapy apparatus, a display for patient 40 which displays various kinds of data about thermotherapy of the patient 1 himself/herself during treatment for the patient 1, and an operation controller for doctor 50 which operates actions of each part of the thermotherapy apparatus.

Hereinafter, the configuration of each part of the thermotherapy apparatus will be described.

The Configuration of the Bed for Thermotherapy:

The bed for thermotherapy 10 is configured to comprise a bed part 10A on which the patient 1 as the subject to be treated lies down and a bed supporting part 10B for liftably/lowerably and horizontally movably supporting the bed part 10A.

As to a Bed Part Entering/Leaving Means:

FIG. 2 is a cross-section diagram schematically showing an internal structure of the bed part 10A, the bed for thermotherapy 10 comprises a bed part entering/leaving means 11 in the bed part 10A, and the bed part entering/leaving means 11 horizontally moves the bed part 10A in its longitudinal direction with respect to an installation surface (i.e. a floor surface). The bed part entering/leaving means 11 is a means for putting the bed part 10A into the gantry 20 or taking out the bed part 10A from the gantry 20, and is configured to employ a servomotor and horizontally move the bed part 10A by its drive control in this embodiment.

As to a Bed Part Lifting/Lowering Means:

FIG. 3 is a cross-section diagram schematically showing the configuration of the bed supporting part 10B, the bed for thermotherapy 10 comprises a bed part lifting/lowering means 12 in the bed supporting part 10B, and the bed part lifting/lowering means 12 lifts/lowers the bed part 10A in the vertical direction with respect to the floor surface. The bed part lifting/lowering means 12 is a means for patient lifting/lowering to reduce burdens of the patient 1's getting in/out of the bed part 10A, and in this embodiment, is configured to comprise "a pantographic arm type lifting/lowering device" which horizontally lifts/lowers the bed part 10A through pantographic arms (X-shaped arms) as the bed part lifting/lowering means 12 instead of the hydraulic cylinder conventionally employed and enable the lowest height of the bed part 10A (a height from the floor surface in a state of maximally lowering the bed part 10A to a bed part upper surface) to lower to about 500 mm (in this embodiment, 540 mm).

"The pantographic arm type lifting/lowering device" referred to here means a device which lifts/lowers a table part by opening/closing the pantographic arms by a thrust of the cylinder installed between the pantographic arms (the X-shaped arms), and is a pantographic arm type table lifter such as Scissor Lift (registered trademark).

Here, a bed part lifting/lowering means (a therapy table lifting/lowering means) conventionally employed in the thermotherapy apparatus will be described.

Figure 12:
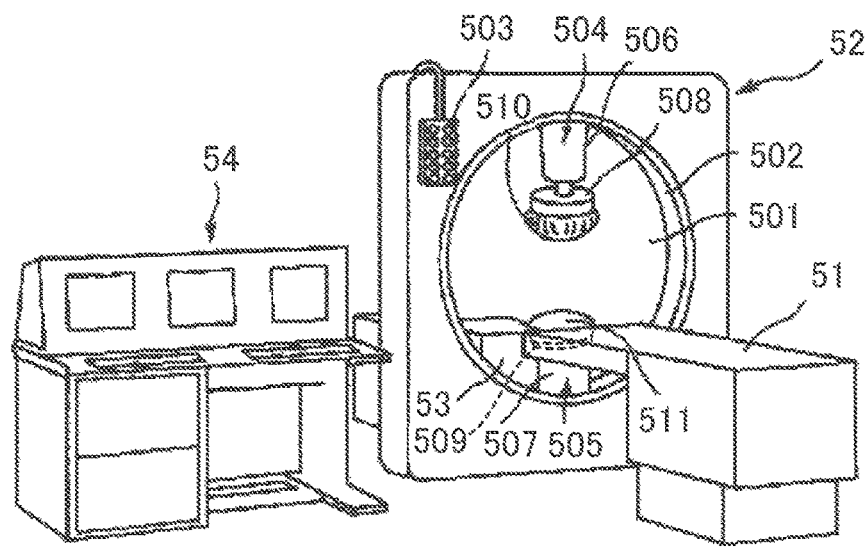
FIG. 12 is an appearance diagram showing one example of a conventional thermotherapy apparatus.

The conventional bed part lifting/lowering means comprises a hydraulic cylinder which supports the therapy table 51 exemplified in FIG. 12 from the vertical direction as a lifting/lowering means, and pushes the therapy table 51 up to the center of the gantry (a height of a therapy table upper surface from the floor surface is about 900 mm) by the hydraulic cylinder. Accordingly, in the conventional thermotherapy apparatus, the lowest height of the therapy table 51 becomes a value obtained by totaling the length of the cylinder during contracting, the height of casters and the thickness of the bed part, even in the case of maximally lowering the therapy table 51, the height can only lower to about 770 mm being the above total value (refer to Non-Patent Document 1).

For example, as shown in an attached document "average value data of 57 items" of "size-JPN2004-2006 as to survey results" published by Ministry of Economy, Trade and Industry on Oct. 1, 2007, an average inside leg height of Japanese males (in their 20's to 70's) is 722 to 784 mm, and an average inside leg height of Japanese females (in their 20's to 70's) is 655 to 723 mm. Hence, in the conventional thermotherapy apparatus that the height can only lower to about 770 mm (a height higher than the average inside leg height of Japanese females), patient's getting in/out of the therapy table 51 is not easy.

On the other hand, in this embodiment, the physical burdens of the patient's getting in/out of the therapy table are reduced by lowering a most-lowered height of the bed part 10A to about 500 mm (in a practical example, 540 mm) by means of the pantographic arm type table lifter (a lifting/lowering device having a link folding mechanism). Further, since it becomes possible to prevent injuries due to a fall when getting out of the bed part 10A, safety is improved. Moreover, a most-lifted height after the patient gets in the bed part 10A is about 900 mm, just like the conventional lifting/lowering means.

As to a Bed Surface Flatization Means:

Next, the bed surface flatization means which is provided in the bed part 10A will be described. Before describing the configuration of the bed surface flatization means, a relation between affected part's treatment aspects and a shutter for opening/closing an opening part (an opening part for lower electrode pass) which is provided in the bed part 10A will be described.

The Relation Between the Treatment Aspects and the Shutter:

As the affected part's treatment aspects of the patient, from a viewpoint of arrangement of the electrode parts 24, there are a treatment aspect (for convenience of explanation, hereinafter referred to as "a first treatment aspect") that treats by means of a vertical direction's high frequency from a pair of the electrode parts 24 (24A, 24B) which sandwich the patient 1 and are disposed so as to be opposite to each other up and down in a state that the patient 1 is in an upward facing/downward facing position (the supine position or the prone position), and a treatment aspect (for convenience of explanation, hereinafter referred to as "a second treatment aspect") that treats by means of a horizontal direction's high frequency from the pair of electrode parts 24 (refer to a dashed line part 24 of FIG. 3) which sandwich the patient 1 and are disposed so as to be opposite to each other left and right in a state that the patient 1 is in a laterally facing position (a right lateral recumbent position or a left lateral recumbent position).

A circular or rectangular opening part (for convenience of explanation, hereinafter also referred to as "the opening part for lower electrode pass") having a size that the electrode part 24B (a lower electrode) shown in FIG. 1 in the first treatment aspect can pass, is formed at a predetermined position of the bed part 10A, and the bed part 10A is provided with the shutter as a means for opening/closing the opening part for lower electrode pass (in this embodiment, a servomotor type shutter).

In the first treatment aspect, after the patient 1 gets in the bed part 10A in a state that the opening part for lower electrode pass is closed and lies down on the bed part 10A in the upward facing/downward facing position, a shutter part is housed within an internal space of the bed part 10A by operating the shutter by the operation of the operation controller for doctor 50 so as to lower the shutter part by a predetermined distance and concurrently move the shutter part horizontally by a predetermined distance in the longitudinal direction of the bed part 10A, accordingly, the opening part for lower electrode pass is opened. And then, after expanding the electrode part 24B (the lower electrode) from below the opening part for lower electrode pass to a position of the bed part upper surface in that state, the electrode part 24A is expanded from above the bed part 10A, and the electrode part 24B and the electrode part 24A of the upper side of the patient are adhered tightly to the body surface of the patient 1 by an electrode pad tightly-adhering means which will be described later.

On the other hand, in the second treatment aspect, just like the first treatment aspect, after the patient 1 gets in the bed part 10A in the state that the opening part for lower electrode pass is closed and lies down on the bed part 10A in the laterally facing position, the electrode parts 24A and 24B respectively located in left and right sides of the patient 1 are expanded toward the patient 1, and the electrode parts 24A and 24B are adhered tightly to the body surface of the patient 1 on the bed part (the patient in the laterally facing position) by the electrode pad tightly-adhering means which will be described later.

Here, a driving mechanism of the shutter will be described.

Figure 4A:
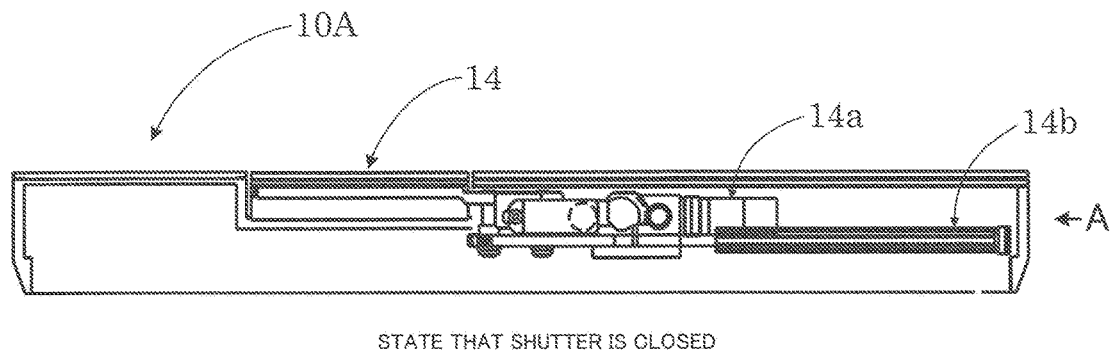
FIGS. 4A and 4B are diagrams schematically showing a driving mechanism of a shutter of the bed part according to the present invention.
Figure 4B:
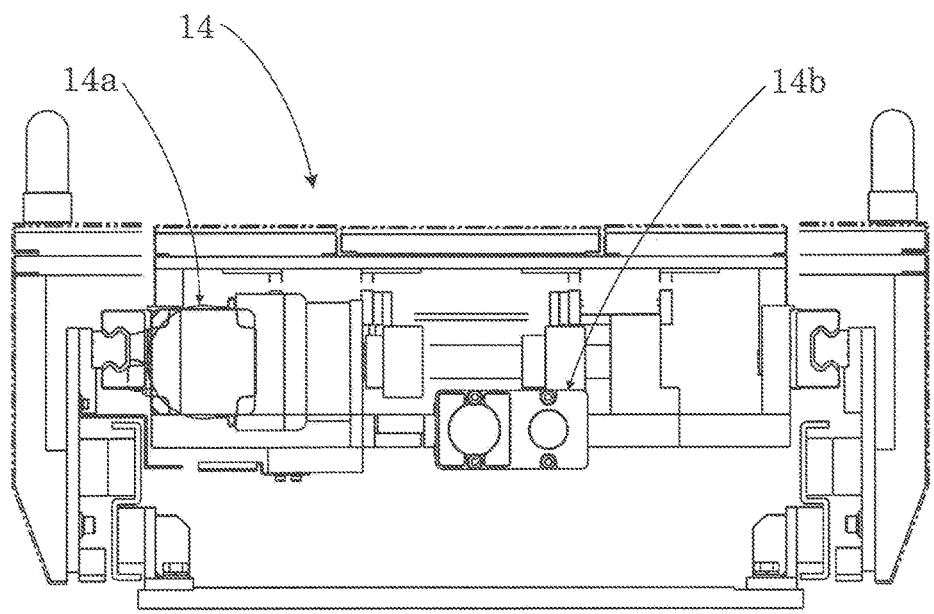

FIGS. 4A and 4B show the driving mechanism of a shutter 14 for opening/closing the opening part of the bed part 10A, FIG. 4A is a side part cross-section diagram of the bed part 10A, and FIG. 4B is an A-arrow view viewing driving parts (14a, 14b) of FIG. 4A from an arrow A direction.

In FIGS. 4A and 4B, the shutter 14 is an electric shutter that works in accordance with the operation of the operation controller for doctor 50, and comprises a shutter lifting/lowering servomotor 14a and a shutter running servomotor 14b as its driving mechanism.

The shutter lifting/lowering servomotor 14a is a servomotor for making the shutter (a lid body) 14 located in the opening part of the bed part 10A to run in the up and down directions (the vertical direction) with respect to a bed surface, and the shutter running servomotor 14b is a servomotor for making the shutter (the lid body) 14 to run along a guide member in the inside of a housing of the bed part 10A in a longitudinal direction of the bed surface (the horizontal direction).

This embodiment comprises the bed surface flatization means that flatizes a level difference in the bed surface (an upper surface of the bed part 10A) which occurs in a state that the shutter 14 described above is closed.

Figure 6A:
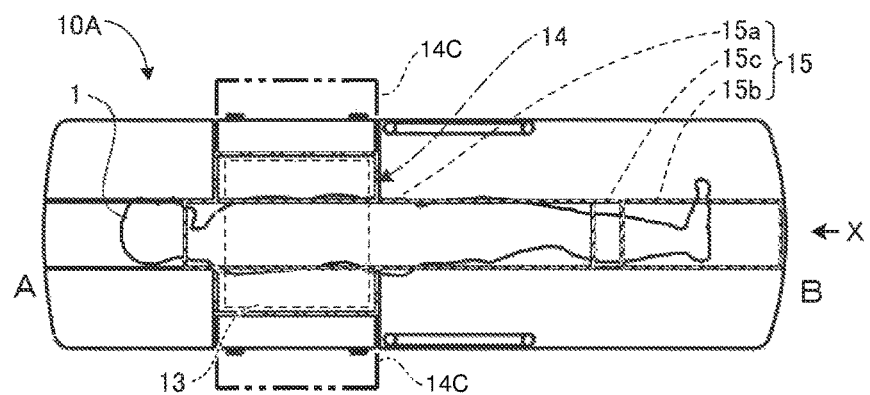
FIGS. 6A, 6B, 6C and 6(D) are diagrams for explaining the bed surface flatization means according to the present invention.
Figure 6C:
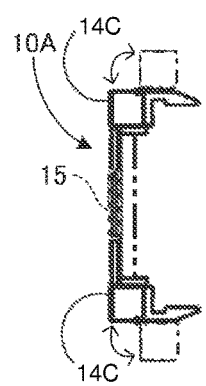
Figure 6B:
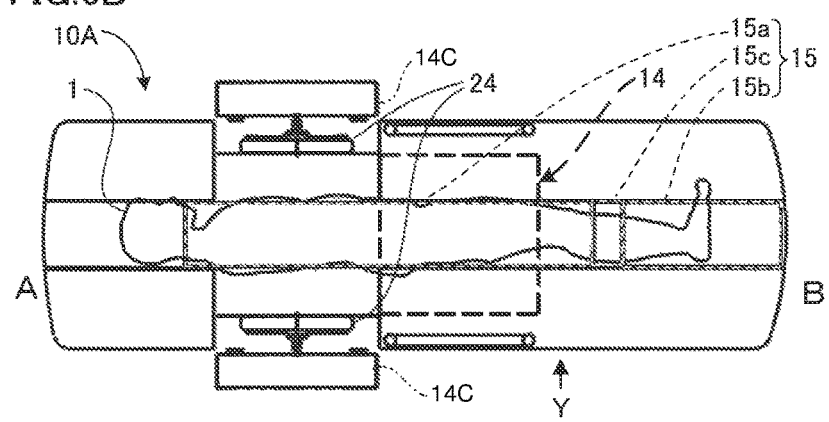
Figure 6D:
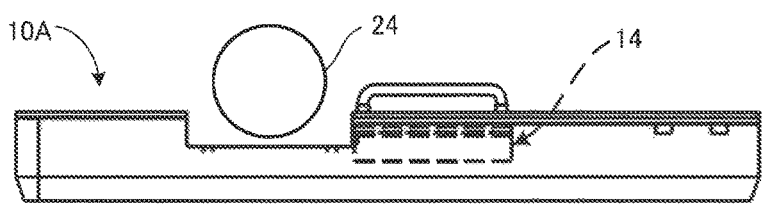

The Configuration of the Bed Surface Flatization Means:

FIGS. 5A, 5B, 5C, FIGS. 6A, 6B, 6C and 6D are schematic diagrams for explaining the configuration of a bed surface flatization means 15, FIGS. 5A, 5B and 5C show an arrangement configuration of the bed surface flatization means 15 in the first treatment aspect (in this practical example, slide type tables 15a, 15b and 15c), and FIGS. 6A, 6B, 6C and 6D show an arrangement configuration of the bed surface flatization means 15 in the second treatment aspect. Further, FIGS. 5A, 5B, 6A and 6B are plan views of the bed part 10A comprising the bed surface flatization means 15, FIGS. 5C and 6C are sectional views respectively viewing the bed part 10A of FIG. 5A and the bed part 10A of FIG. 6A from an arrow X direction, and FIG. 6D is a side sectional view viewing the bed part 10A of FIG. 6B from an arrow Y direction. Moreover, parts shown in FIGS. 5A, 6A, 6B and 6C by a reference numeral 14C are a member (referred to as "a side cover") which is freely turnable toward below the bed part 10A (the shutter part) in the laterally facing treatment, and the side cover 14C is a member for avoiding interference with a large diameter electrode during the laterally facing treatment.

The bed surface flatization means 15 is a means for mattress substitute that is substituted for the mattress which is laid on the upper surface of the therapy table part in the case of the second treatment aspect in the conventional apparatus, and the means for mattress substitute is a means which slides the bed part upper surface in its longitudinal direction and flatizes the bed part upper surface.

In this embodiment, the bed surface flatization means 15 is configured to comprise the slide type tables 15a, 15b and 15c which are slidable in the longitudinal direction of the bed part 10A.

Concretely, in this embodiment, the bed surface flatization means 15 is configured to comprise a rectangular slide table that comprises the first division table (an opening part sliding connecting table) 15a that a length in the longitudinal direction of the bed part 10A is longer than a length of the shutter 14 (a diameter of the opening part) and the second division table (a shutter interlock table) 15b that the length in the longitudinal direction of the bed part 10A is the same as the length of the shutter 14, and is capable of changing the arrangement in the longitudinal direction of the bed part 10A of the first division table 15a and the second division table 15b.

Furthermore, in this embodiment, the rectangular slide table as the bed surface flatization means 15 further comprises the third division table 15c for filling an empty space which is formed when the first division table 15a and the second division table 15b are arranged at predetermined positions of the bed part upper surface.

The second division table 15b is a table which works with the shutter 14 located in both sides of the second division table 15b (both end parts of the second division table 15b in a width direction of the bed part 10A) as a shutter part which blocks an opening part for lower electrode pass 13 (in this practical example, the shutter part that a cross-sectional shape in the width direction of the bed part 10A becomes a rectangular shape in a state that the second division table 15b is fitted in a recessed part of the shutter that the cross-sectional shape is a recessed shape) in the case of the first treatment aspect.

The bed part 10A, these slide tables 15a, 15b and 15c and the shutter 14, are comprised of members having elasticity such as resin material and rubber material (for example, polyvinyl chloride sheets, sponges and lumbers), and relieve pains in the case that the patient keeps the recumbent position over a long time in comparison with a conventional therapy table having the toughness.

As to Opening/Closing Operation of the Shutter Part in the First Treatment Aspect:

Here, the opening/closing operation of the shutter part which is comprised of the shutter 14 and the second division table 15b will be described with reference to FIGS. 5A, 5B and 5C.

In this embodiment, in the case of the first treatment aspect, the patient lies down on the bed part 10A in a state that the slide tables 15a, 15b and 15c are arranged as shown in FIGS. 5A, 5B and 5C (in a flat state that there is no level difference in a whole area of the upper surface of the bed part), and then, at the time of the opening operation of the shutter 14 during performing the treatment, as shown in FIG. 5B, it is configured that the second division table 15b is united with the shutter 14 and housed in a lower part (an internal void part) of the bed part 10A by horizontally moving the second division table 15b and the shutter 14 to B side shown in FIG. 5A by drive control of the shutter running servomotor 14b exemplified in FIG. 4 after lowering the second division table 15b and the shutter 14 in the vertical direction by drive control of the shutter lifting/lowering servomotor 14a exemplified in FIG. 4.

On the other hand, at the time of the closing operation of the shutter 14 when the treatment using the electrode parts 24 in a state shown in FIG. 5B is finished, a level difference in the bed surface which occurs in a state that the shutter is closed in the conventional thermotherapy apparatus, is flatized by employing a configuration of uniforming the height with a shutter part upper surface and the bed part upper surface by lifting the second division table 15b and the shutter 14 to a position of the bed part upper surface (the upper surface of the bed part 10A) in the vertical direction by the drive control of the shutter lifting/lowering servomotor 14a exemplified in FIG. 4 after horizontally moving the second division table 15b and the shutter 14 to A side shown in FIG. 5B by the drive control of the shutter running servomotor 14b exemplified in FIG. 4.

And then, the bed part 10A is lowered by the bed part lifting/lowering means 12 described above before the patient gets out of the bed part 10A.

As to Arrangement of the Slide Tables in the Second Treatment Aspect:

Next, the arrangement configuration of the slide tables 15a, 15b and 15c in the second treatment aspect will be described with reference to FIGS. 6A, 6B, 6C and 6D.

This embodiment makes electrodes having a size which exceeds 300 mm being the maximum diameter size of the electrode used in the conventional thermotherapy apparatus available. Although the details will be described later, this embodiment can perform a treatment using the electrode which is an electrode plate for performing the dielectric heating with respect to an extensive region of the patient and has a size (the diameter size) at the same level as the horizontal width of the human body of the average adult (an electrode that a diameter $\varphi$ of a circular electrode plate is approximately 400 mm and a diameter size including a bulge of a pad part (an electrode pad) attached on the electrode plate is about $\varphi$ 460 mm, is preferred).

Furthermore, "the horizontal width of the human body of the average adult" referred to in the present invention means an average value of thoracicoabdominal parts (acromion intervals or widths of abdomens) of adults and for example, corresponds to an average "acromion interval" by age of Japanese (in their 20's to 70's) shown in the attached document "average value data of 57 items" of "size-JPN2004-2006 as to survey results" published by Ministry of Economy, Trade and Industry on Oct. 1, 2007. In the attached document, the average "acromion interval" of Japanese (in their 20's to 70's) is within a range from 347 mm to 406 mm. Here, 347 mm is an average value of Japanese females aged 75-79 being a minimum average value among average values by age, and 406 mm is an average value of Japanese males aged 30-39 being a maximum average value among the average values by age.

As a result, it is preferred that the diameter $\varphi$ of the electrode plate is within a range of "approximately 350 mm to 410 mm" being the horizontal width of the human body of the average adult or is set to about the maximum average value of the horizontal width's range. Accordingly, in this embodiment, the diameter $\varphi$ of the electrode plate is set to 400 mm being an approximately maximum average value among the average values of "acromion interval" by age, and it is possible to generate an electromagnetic field that the diameter $\varphi$ exceeds 400 mm.

In this embodiment, the shutter of the opening part 13 is also enlarged with the enlargement of the electrode size, and the size of the opening part 13 is set to a size that exceeds the diameter size of the electrode part 24 ("the diameter size including the bulge of the pad part of the electrode part 24"+"a size of an empty space between a side surface of the pad and a side surface of the opening part"). Hence, in the second treatment aspect that the patient receives treatment in the laterally facing position, in the case of a conventional handling that the mattress is spread out on the shutter having the same material and thickness as the conventional one, there is a possibility that a force is also applied to the part of the shutter during treatment and a problem of strength occurs.

Therefore, in this embodiment, in the case of the second treatment aspect that the patient receives treatment in the laterally facing position, as shown in FIG. 6A, by employing a configuration that disposes the first division table 15a in a side of the opening part 13 (A side shown in FIG. 6A), disposes the second division table 15b in a side where the opening part 13 is not provided (B side shown in FIG. 6A), and is capable of installing the first division table 15a across both sides of the opening part 13 (bridging the first division table 15a over slide table supporting members of both sides of the opening part 13), the problem of strength is prevented from occurring.

Further, these division tables 15a, 15b (and 15c) are configured that respective heights of table upper surfaces have the same height as a height of other upper surface part of the bed part 10A, in this embodiment, by comprising such slide tables (and guide members for slide) as the bed surface flatization means 15, it becomes possible to ensure the body position of the patient without comprising accessories etc. such as a mattress and so on. Further, the shutter 14 in this embodiment also serves as a means for avoiding "the interference of the electrodes with the therapy table" in the case of the treatment based on the high frequency electric field from the lateral direction described in the above problem (1). That is to say, in the case of using the large-sized electrode during the laterally facing treatment, in a state shown in FIG. 6A that the patient 1 is on the first division table 15a (the opening part sliding connecting table), the shutter 14 is operated by the operation of the operation controller for doctor 50 so as to lower the shutter part by the predetermined distance. Or, just like the first treatment aspect, as shown in examples of FIGS. 6B and 6D, the shutter 14 is housed within the internal space of the bed part 10A by lowering the shutter part by the predetermined distance and concurrently moving the shutter part horizontally by the predetermined distance in the longitudinal direction of the bed part 10A.

As described above, by lowering the shutter 14 by the predetermined distance (for example, to a position lower than a lower end of the pad part of "a maximum-sized electrode part 24" during the laterally facing treatment exemplified in FIG. 6D), since parts of right and left sides of the first division table 15a shown in FIG. 6C become lower than the upper surface of the table 15a, it is possible to avoid the interference of the pad part of the large diameter electrode 24 during the laterally facing treatment with parts of both sides in the width direction of the bed part 10A. Furthermore, this embodiment is configured that plate-like side covers 14C that cover side parts of the bed part and are capable of concurrently opening/closing the side parts of the bed part by manual operation (in this example, as shown in FIG. 6C, the side covers 14C which are 180-degree freely turnable from the vertical direction), are provided on both sides of the shutter 14 in the longitudinal direction of the bed part. By turning the side covers 14C toward below by manual operation, as shown in FIG. 6B, spaces are formed at the parts of both sides in the width direction of the bed part 10A, accordingly, a configuration avoiding the interference of the pad part of the large diameter electrode 24 during the laterally facing treatment with the side covers 14C is obtained.

By comprising the shutter 14 and the bed surface flatization means 15 described above, it becomes possible to apply the large-sized electrode, concurrently the mattress storage space becomes unnecessary and it becomes possible to use the space used for the mattress storage space for other purposes. Further, since carrying around of the mattress and the mattress laying work become unnecessary and only setting by the slide tables is necessary, the burdens on the doctor are reduced. Moreover, in this embodiment, in any one of the first treatment aspect and the second treatment aspect, when the patient gets on/off, since a bed surface of the bed for thermotherapy 10 becomes flat, it is possible to safely get on/off without misstep etc. caused by a level difference in the bed surface which occurs conventionally.

The Configuration of the Gantry:

Next, the configuration of the gantry 20 will be described.

Figure 7:
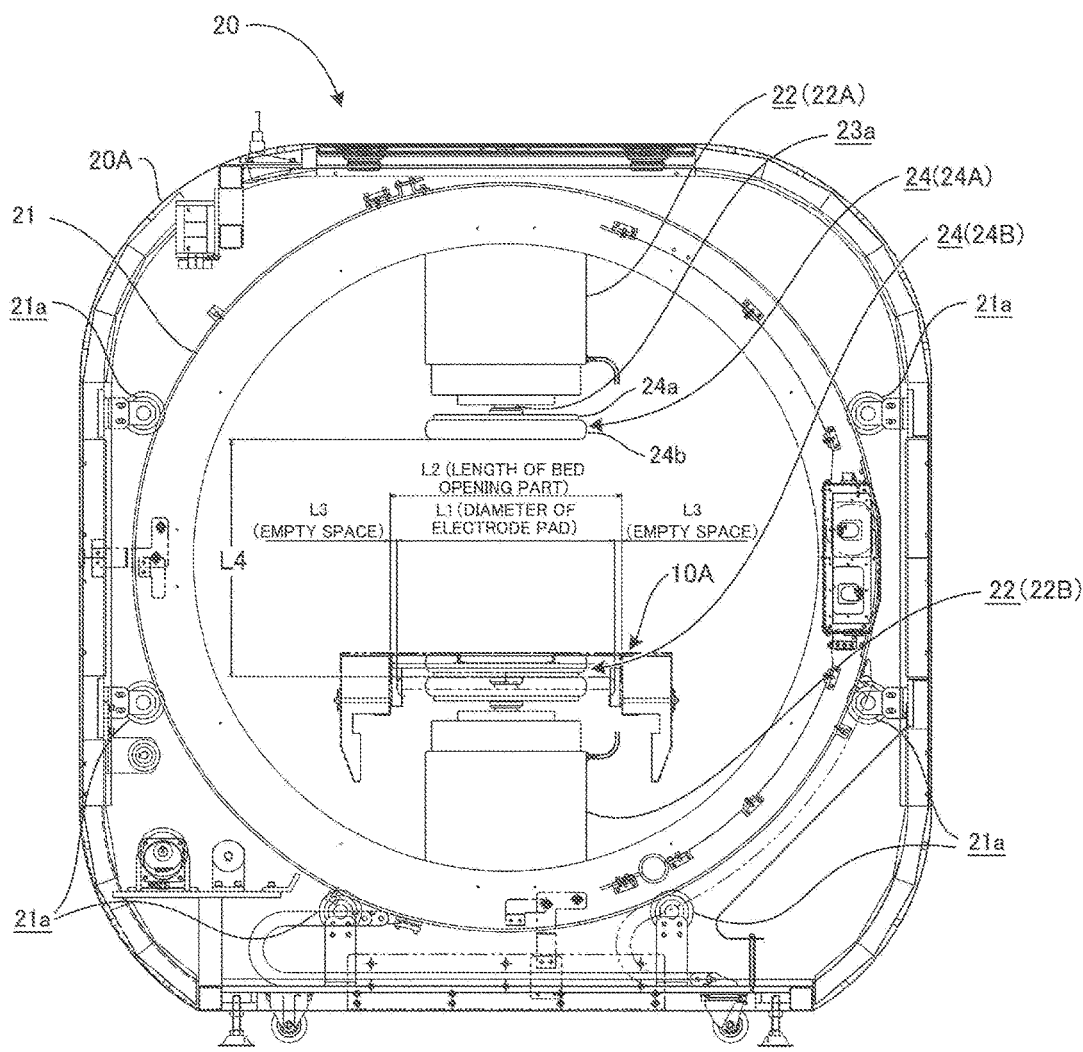
FIG. 7 is a partial cross-section structural diagram schematically showing a configuration of a gantry according to the present invention.

FIG. 7 is a partial cross-section structural diagram schematically showing the configuration of the gantry 20. As shown in FIG. 7, the gantry 20 is configured to comprise a rotating ring 21 which is pivotably supported via a roller 21a (a supporting roller) circumferentially provided within its housing and can control so as to pivot around the patient on the bed part 10A with setting a direction parallel to the longitudinal direction of the bed part 10A as an axis, a pair of expanding/contracting arms (arms for electrode mounting) 22 (22A, 22B) which are disposed so as to protrude from an inner peripheral surface of the rotating ring 21 in a ring center direction and be opposite to each other and can control so as to expand/contract in a diameter direction of the rotating ring 21, spherical joints 23a which are provided on tip parts of the expanding/contracting arms 22 (in this example, spherical joints having sphere parts fitted in spherical recessed parts formed on the tip parts of the expanding/contracting arms 22), and the electrode parts 24 (24A, 24B) which are tiltably supported in an arbitrary direction via the spherical joints 23a.

In this embodiment, a diameter L1 of an electrode pad 24b is set to 460 mm, and a length L2 (L2=L1+L3×2) of a bed opening part (the opening part for lower electrode pass 13) is set to 588 mm (where L3 represents a length of an empty space between a side surface of the electrode pad 24b and a side surface of the bed opening part). Further, a length L4 between a pair of the electrode pads 24b is set to 500 mm (where L4 represents the length between the pair of the electrode pads 24b when expanding the electrode part 24B located below the bed part 10A and lifting the electrode part 24B to near the upper surface of the bed part 10A, and concurrently expanding the electrode part 24A located above the bed part 10A by the same distance and lowering the electrode part 24A to the bed part 10A side).

Further, in order to prevent the emission of spreading electromagnetic waves, in this embodiment, it is configured that a width in a depth direction of a rotating drum (the rotating ring 21) is set to 440 mm (or a size which exceeds 440 mm) in accordance with 400 mm being a maximum diameter size of an electrode plate 24a and the rotating drum is a rotating drum made of aluminum. Furthermore, it is configured that a shielding plate 20A made of aluminum is stuck on an inner face of an exterior of a gantry frame (a housing of the gantry 20). Moreover, although it is preferred that the rotating ring 21 and the shielding plate are made of aluminum, it is also possible to use other materials having a shielding function of electromagnetic waves generated by high frequency (for example, Permalloy) as a substitute for aluminum.

In this way, for an active measure to improve the therapeutic effects, this embodiment i-s-configured such that the electrode plate 24a having the diameter size of approximately the horizontal width of the human body of the common adult (for example, about 400 mm) is made available, by applying the electric force line to a broad area around the affected part, in comparison with the conventional thermotherapy apparatus, the cancer stem cells having the possibility of attracting extensive metastases can be necrotized by further improving the immunity of the wide range of normal cells on the periphery of the affected part.

Figure 8:
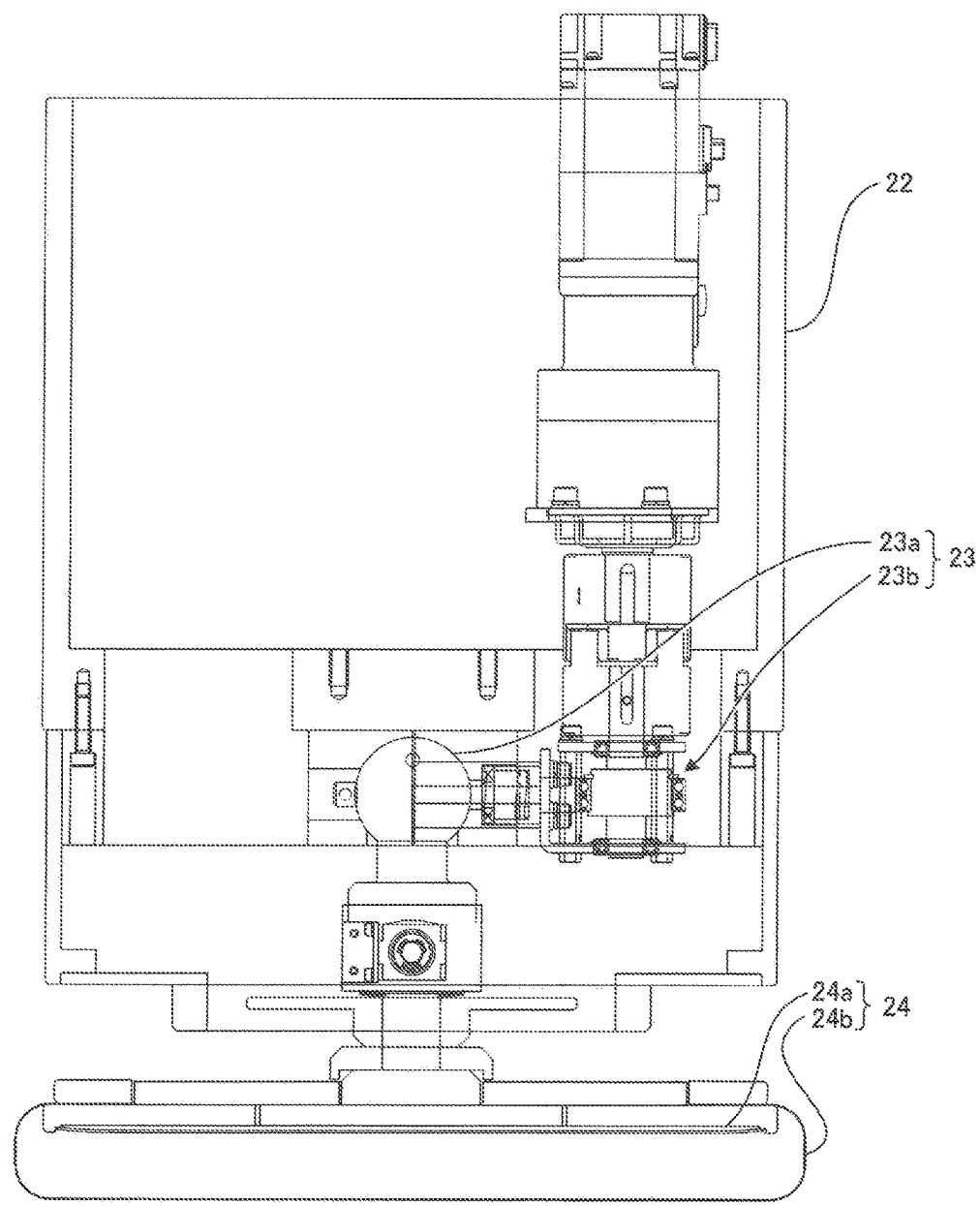
FIG. 8 is a first diagram schematically showing a configuration of an electrode pad tightly-adhering means according to the present invention.
Figure 9:
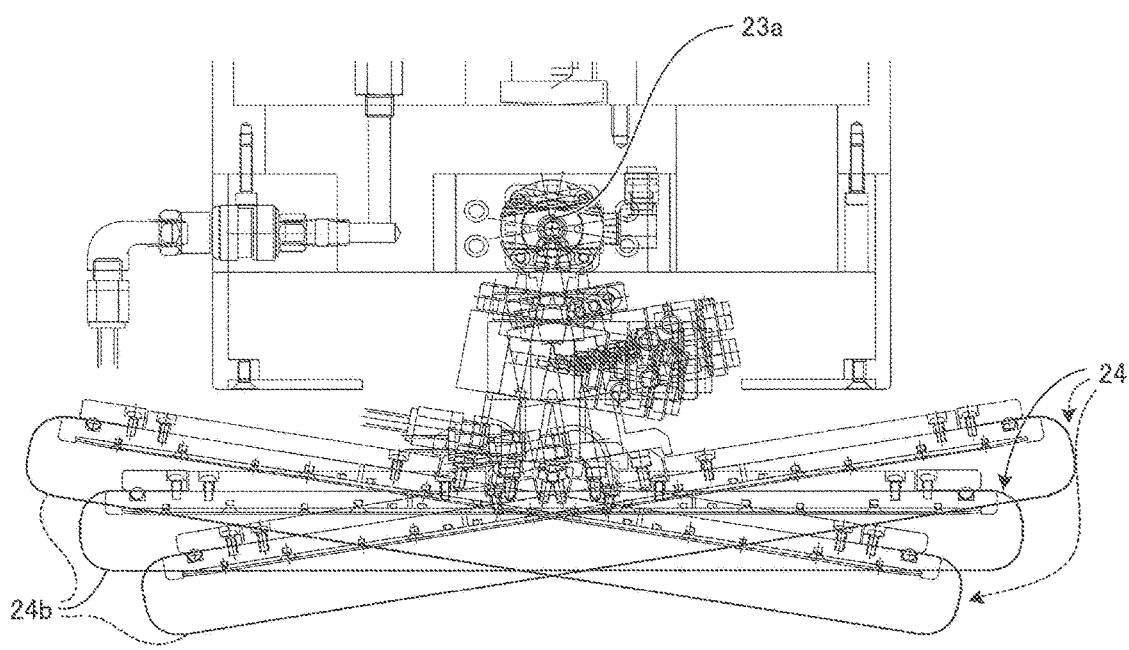
FIG. 9 is a second diagram schematically showing the configuration of the electrode pad tightly-adhering means according to the present invention.

As to the Electrode Pad Tightly-Adhering Means:

FIG. 8 and FIG. 9 are partial cross-section structural diagrams schematically showing the configuration of the electrode pad tightly-adhering means according to the present invention.

As described in "(2) reduction of adhesiveness of an electrode surface to a body surface of the patient" which is a problem to be solved by the present invention, when the diameter size of the electrode plate is enlarged to the size of approximately the horizontal width of the human body of the common adult, it is considered that the adhesiveness to the body surface of the patient gets worse and the incident quantity of the electric force line into patient's body decreases.

Therefore, the thermotherapy apparatus according to the present invention is configured to comprise the electrode pad tightly-adhering means which makes a pad surface of the electrode part adhere tightly to the body surface of the patient.

As shown in FIG. 8, an electrode pad tightly-adhering means 23 is configured to comprise the spherical joints 23a which tiltably support the electrode parts 24 (24A, 24B) in an arbitrary direction, an electrode angle fixing means 23b for fixing a tilting angle of the electrode part 24 in a state that makes the pad surface of the electrode part adhere tightly to the body surface of the patient in accordance with a tilt fixing operation performed by the doctor and a pad surface which is made of a soft material.

The expanding/contracting arm 22 provided in the rotating ring 21 of the gantry 20 exemplified in FIG. 7 is configured that as shown in FIG. 8, the tip part of the expanding/contracting arm 22 is fitted in the spherical joint 23a mounted on the electrode part 24. Further, in a state of not performing the tilt fixing operation by means of the operation controller for doctor 50 (refer to FIG. 1), as shown in FIG. 9, it is configured that the electrode part 24 tilts in an arbitrary direction via the spherical joint 23a and its tilting direction and tilting angle can be adjusted.

The electrode angle fixing means 23b is a means for fixing the above tilting angle (and tilting direction), and for example, this means is configured by a rotating clamp mechanism driven by a servomotor capable of performing a pressurizing action to the spherical joint 23a and a separating action from the spherical joint 23a by button operations (switch operations).

Figure 10:
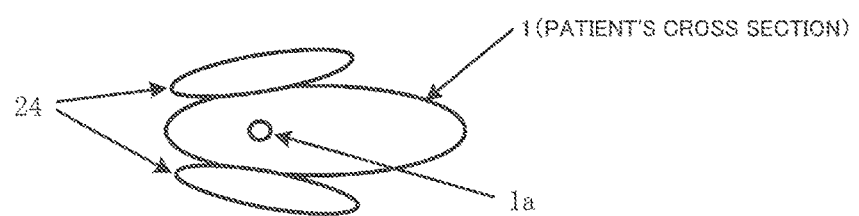
FIG. 10 is a schematic diagram for explaining the electrode pad tightly-adhering means according to the present invention.

In the example of FIG. 8, the electrode angle fixing means 23b is configured by a compression spring and an eccentric cam. Further, as shown in the schematic diagram of FIG. 10, in a state of lightly pressing the electrode part 24 against the patient 1, when the doctor pushes a clamp button (for example, a button provided on a clamp mechanism part or the operation controller for doctor 50), since the eccentric cam pushes the spring and pushes the spherical joint 23a in accordance with the operation performed by the doctor, the fixing of the tilting angle is completed. Further, the electrode pad 24b (refer to FIG. 8) for heating a broad area (about φ400 mm) including an affected part 1a of the patient 1 is a pad which is attached on a surfaces of the electrode plate 24a (the surfaces spliced on the living body) and is capable of performing cooling and warming control, and this electrode pad 24b includes liquid (hereinafter, the liquid is water) and is formed so as to cover the surfaces of the electrode plate 24a with an elastically deformable member in accordance with the shape of the body surface of the patient.

In other words, also, the electrode pad 24b is a component of the electrode pad tightly-adhering means 23.

By comprising the electrode pad tightly-adhering means 23 having the configuration described above, it becomes possible that the electrode part 24 is adhered more tightly to the body surface of the patient 1 and the electrode is more certainly applied to the body surface of the patient 1. Consequently, in the thermotherapy apparatus according to the present invention, it is possible to make more stable and more electric force line incident into the patient's body, and concurrently it becomes possible to improve the uncertain tightly-adhering state between the electrode and the body surface of the patient.

The Configuration of the High Frequency Generation and Control Part:

The high frequency generation and control part 30 is a part which controls the drive of each part of the thermotherapy apparatus, and comprises a high frequency generating device, an impedance measuring device, a pad temperature adjusting device, a temperature measuring device, a computer for control and so on.

The high frequency generating device is a device which comprises a power supply circuit, a high frequency oscillator, a matcher, a high frequency wattmeter and so on. The impedance measuring device is a device which measures an impedance between electrodes as a living body impedance from a voltage value applied between the electrodes which sandwich the living body and a current value flowing between the electrodes. Further, the temperature measuring device is a device which removes high frequency noises superimposed on temperature data measured by a temperature sensor by using a filter comprised of a toroidal coil and a condenser and measures a temperature having a small error.

For example, a thermocouple is used as the above temperature sensor. Further, the temperature measuring device removes high frequency noises included in a signal from the thermocouple via for example a low-pass filter and outputs the signal after removing the high frequency noises (an affected part's temperature measurement signal) to the temperature adjusting device and PLC (or an external computer) via a couple converter. In other words, the temperature measuring device comprises a means for reducing the error of the temperature sensor caused by the influence of the high frequency of the thermotherapy apparatus and can accurately perform the affected part's temperature measurement.

The computer for control of the high frequency generation and control part 30 performs a temperature control of a living body (an affected part within the living body and its peripheral part) based on an output control of a high frequency energy amount, a temperature control of the pad part 24b of the electrode part 24, a lifting/lowering and horizontally moving control of the bed part 10A of the bed for thermotherapy 10, an opening/closing control of the opening part for lower electrode pass 13 by the shutter 14, a pivoting control of the rotating ring 21 of the gantry 20, an expanding/contracting control of the expanding/contracting arm 22 on which the electrode part 24 is attachably/detachably mounted and so on.

Moreover, since the high frequency generating device and the impedance measuring device are publicly known devices used in the conventional thermotherapy apparatus, their detailed explanations will be omitted. Further, since a basic technique that performs the dielectric heating with respect to the affected part by means of the high frequency electric field is the same as the conventional thermotherapy apparatus, its detailed explanations will also be omitted.

Hereinafter, an improved technique of the high frequency generation and control part 30 will be described.

The Configuration of the Pad Temperature Adjusting Device:

The pad temperature adjusting device comprises "a circulating device" which circulates water between the electrode pad 24b contacting with the living body (hereinafter, also referred to as "a pad for body surface temperature adjustment") and a storage tank, "a temperature adjusting means" which can control so as to adjust the temperature of water which flows within the above pad for body surface temperature adjustment 24b, and so on.

The temperature adjusting means of the pad temperature adjusting device, for example, comprises an electromagnetic valve for switching between cold water from a cold water tank for generating cold water and warm water from a warm water tank for generating warm water, and switches cold water and warm water of water which flows within the pad 24b based on a control performed by the computer for control, for example, on the basis of a temperature control signal from the external computer based on operations of a temperature regulator provided within the high frequency generation and control part. In this case, in this embodiment, the temperature adjusting means is configured that at first, a state of warming the temperature of the pad 24b (in this example, the temperature of water which flows within the pad) or a state of cooling the temperature of the pad 24b is set without setting a state of lowering the temperature by cooling from the beginning so that the patient's body temperature is within a normal body temperature (within around 36.5 degrees Celsius or within a normal body temperature of an individual patient), after bringing the pad into contact with the body surface of the patient in that state, switching of warm water and cold water is performed in accordance with a manual switching operation. For example, in the case of winter season, when expanding the electrode part and bringing the pad into contact with the body surface of the patient, by performing operations so as to bring into contact with the body surface in a state of circulating warm water having a higher temperature than other seasons (summer season and intermediate season) and then lower the temperature from a point of time when performing the dielectric heating with respect to the affected part or a point of time slightly earlier than the point of time when performing the dielectric heating with respect to the affected part to suppress temperature rise of the body surface, it becomes possible to relieve the thermal pains inflicted on the patient.

Further, in this embodiment, the pad temperature adjusting device is configured to switch cold water (or refrigerant gas) and warm water respectively and separately to be capable of supplying to a pair of electrode pads 24b provided in the electrode parts 24A and 24B exemplified in FIG. 7, and further realizes the temperature setting that is the most desirable for the patient by separately controlling the temperature control of fluid (cold water or warm water) which flows in one electrode pad 24b and the temperature control of fluid (cold water or warm water) which flows in the other electrode pad 24b.

Further, the pad temperature adjusting device comprises a circulating device which constantly maintains a pressure of fluid (cold water or warm water) within the electrode pad 24b at a weak constant pressure, and in order to confirm that fluid circulates, this circulating device is configured to comprise an instrument (a flow rate measuring instrument) which monitors the flow rate of fluid supplied to the electrode pad 24b.

Furthermore, the thermotherapy apparatus according to the present invention comprises a pressure measuring instrument which measures the pressure of fluid drained from the electrode pad 24b and a means for detecting a pressing force of the electrode pad 24b against the body surface of the patient (a pressing force detecting means such as a servo-motor torque limiting function, a sensor) as a means for monitoring abnormality in the above pressing force.

This embodiment is configured that the above pressure measuring instrument is provided in the circulating device and the above means is provided in an expanding/contracting mechanism built in the expanding/contracting arm 22 (refer to FIG. 7) of the electrode pad 24b.

Further, for example, it is possible to monitor the pressing force by a computer based on a detection signal from the above means and a measurement value from the above pressure measuring instrument, in the case of judging that the electrode pad 26b is pressed too much to the patient, the alarm is generated to prevent pressing further (it is possible to release the pressing force). Moreover, with respect to the pressing force, an optimum value is set for every electrode size (a diameter size of each pad), and in the control part of thermotherapy apparatus, the pressure against the body surface of the patient is adjusted in accordance with the size of the electrode pad 26b.

As to the Display for Patient:

The display for patient 40 is a display which is provided at a position where the patient 1 on the bed for thermotherapy 10 under treatment can view (in this example, an upper part of the gantry 20) and is capable of performing pivot and angle changing, and a display control means of the high frequency generation and control part 30 displays information showing the patient's therapeutic situation or videos and audios for appreciation purpose in the display for patient 40.

In this embodiment, information displayed in real time in the display for patient 40 during treatment based on the dielectric heating includes patient's individual information such as instantaneous data of the power of incident waves, an elapsed treatment time and instantaneous data of the temperature sensor.

Moreover, with respect to changing operations of pivot and angle of the display for patient 40, the doctor performs adjustment by manual operations (or, in an aspect comprising a pivot and angle drive device, for example, by drive operations performed by the operation controller for doctor 50) at a position where the patient is easy to look at.

In this way, since the thermotherapy apparatus according to the present invention comprises the display for patient 40 that the patient 1 under treatment can view and is configured to display information showing the therapeutic situation displayed in a display for doctor, in the display for patient 40, it becomes possible for the patient to visually confirm the therapeutic situation of the patient himself/herself during treatment. Further, since the patient can view videos for appreciation purpose or listen to audios for appreciation purpose during treatment, it is possible to reduce the mental burdens on the patient during treatment such as anxious thoughts caused by a matter that the patient does not understand the therapeutic situation at all during the treatment time (for example, 40 minutes) in the case of the conventional thermotherapy apparatus.

Operation Procedures for the Operation Controller for Doctor and Thermotherapy:

Next, operation procedures for the operation controller for doctor 50 and thermotherapy using the operation controller for doctor 50 will be described.

The operation controller for doctor 50 is a controller for doctor that operates actions of each part of the thermotherapy apparatus via the high frequency generation and control part 30 and can perform the following operations by the operation of operation buttons.

Further, although a part of the operation procedures can be linked and automatized, since this embodiment employs an aspect that independently drives each part of the thermotherapy apparatus by button operations of the operation controller for doctor 50, a possibility of the occurrence of accidents due to incorrect operations is reduced as much as possible.

Operations Using the Operation Controller for Doctor 50:
    emergency stop
    abnormality indicating light
    high frequency oscillation indicating light
    tightly-adhering operation of the electrode part to the body surface (expansion of the expanding/contracting arm 22A)
    separating operation of the electrode part from the body surface after treatment ends (contraction of the expanding/contracting arm 22A)
    tightly-adhering operation of the electrode part to the body surface (expansion of the expanding/contracting arm 22B)
    separating operation of the electrode part from the body surface after treatment ends (contraction of the expanding/contracting arm 22B)
    left rotating operation of the rotating ring 21 of the gantry 20 (an irradiation direction: up and down directions or left and right directions of the patient)
    right rotating operation of the rotating ring 21 of the gantry 20 (the irradiation direction: up and down directions or left and right directions of the patient)
    fixing and releasing of swinging (tilting) of the electrode part 24A
    fixing and releasing of swinging (tilting) of the electrode part 24B
    clamp and unclamp of the electrode part 24A
    clamp and unclamp of the electrode part 24B
    lowering operation of the bed part 10A
    lifting operation of the bed part 10A
    moving operation to enter into the gantry 20 of the bed part 10A
    moving operation to leave from the gantry 20 of the bed part 10A
    opening operation of the shutter 14 of the bed part
    closing operation of the shutter 14 of the bed part In this embodiment, with respect to the above operations, a restriction (an interlock) is imposed on each operation. Further, the restriction is monitored by the high frequency generation and control part 30, in the case of judging that it is operated by an operation ignoring the restriction by means of the operation controller for doctor 50, it is also possible to employ an aspect not to accept the operation.

As to Heating Control Based on Record Data about a Living Body Impedance:

Next, the heating control of the high frequency generation and control part 30 will be described.

As described in "(5) problems relating to reducing of burdens on the patient" which is a problem to be solved by the present invention, in the conventional thermotherapy apparatus, when performing the treatment, the temperature of the affected part is directly measured by pricking with the needle-like temperature sensor or the temperature of the affected part within the cavity is measured from the patient's mouth by inserting the temperature sensor into the cavity each time, the supply of high frequency energy is controlled based on the temperature measurement value so that the rise temperature of cancer cells becomes (enters) the predetermined temperature range, and pains due to inserting of the temperature sensor are given to the patient.

Hence, in the thermotherapy apparatus according to the present invention, with respect to a patient having one time of treatment result, by comprising a heating control means which controls the supply of high frequency energy to the electrode part (the electrode plate) based on the record data about the living body impedance before and after treatment measured once without inserting the temperature sensor into the patient's body so that the rise temperature of cancer cells becomes the predetermined temperature range, it becomes possible to avoid the patient's pains due to inserting of the temperature sensor during treatment from the second time.

It is possible to realize the above heating control means by a sequencer which works by program control, in this embodiment, the high frequency generation and control part 30 is equipped with programs which operate a sequencer of the high frequency generation and control part 30 as a data processing means comprising the above heating control means.

Since a measurement technique of the living body impedance is a publicly known technique, its explanation will be omitted. Here, the heating control based on the record data about the living body impedance will be described.

The heating control means controls the supply of high frequency energy to the electrode plate based on a measured temperature having a small error obtained by removing noise of detection data of the temperature sensor (a sensor for detecting the temperature of the affected part) during the first treatment so that the temperature of the affected part becomes a predetermined temperature range. In this case, the heating control means associates measurement data of the living body impedance of the patient and temperature data of the affected part with a patient ID (an identifier for identifying the patient) and records them in a database. "The measurement data of the living body impedance" referred to here means actually-measured data of the impedance of the living body located between electrodes before and after treatment. Further, "the temperature data" referred to here means data showing a time-series change in the temperature of the affected part (actually-measured data using the temperature sensor). The record data shows a correlation between a reached temperature of the affected part of the patient who received thermotherapy and the living body impedance of the patient.

Therefore, the heating control means controls the supply of high frequency energy to the electrode plate based on temperature measurement data so that the temperature of the affected part becomes the predetermined temperature range.

Here, the configuration of the database that the above temperature measurement data are recorded and the data processing means installed on a computer for doctor will be described with reference to FIG. 11.

The thermotherapy apparatus according to the present invention is connected to the computer for doctor via a wired or wireless communication means. Further, the computer for doctor comprises a patient data recording means which associates patient data D exemplified in FIG. 11 with the patient ID and records them in a patient database and a patient data browsing means which displays the patient data D obtained from the patient database in a display part of the computer for doctor as the data processing means.

Figure 11:
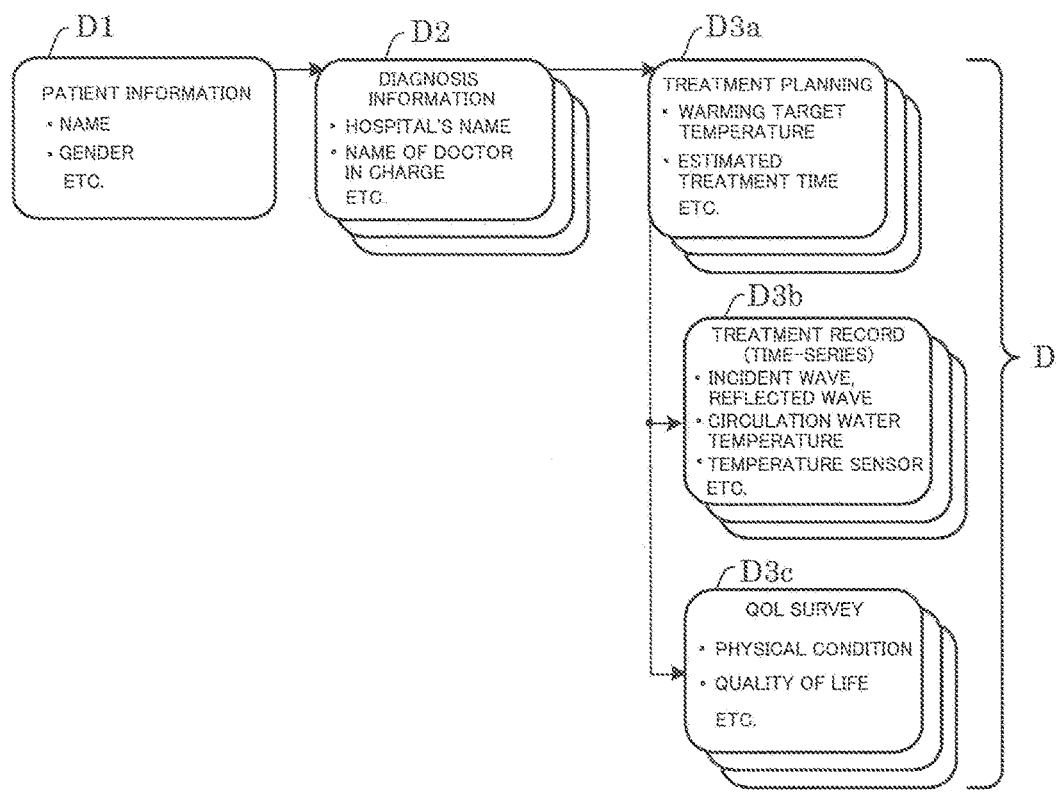
FIG. 11 is a conceptual diagram showing a configuration example of a patient database according to the present invention.

FIG. 11 shows a configuration example of the patient data D relating to thermotherapy, and for example, the patient data D is configured to include patient information D1 (name, gender etc.), diagnosis information of patient by doctor D2 (hospital's name, name of doctor in charge etc.), treatment planning information D3a (warming target temperature, estimated treatment time etc.), treatment record D3b showing various kinds of measurement data during treatment in time series (measurement data such as incident wave, reflected wave, circulation water temperature, temperature sensor etc.) and QOL survey D3c showing survey results (physical condition, quality of life etc.) of QOL (Quality of Life). Further, the doctor scrutinizes records of the patient data D by the computer for doctor and prepares data representing the next treatment planning for patient, and then the prepared data are reflected on the patient database as the treatment planning information D3a. Further, in performing the next treatment with respect to the patient, the control means of the thermotherapy apparatus controls a heating temperature of the affected part of the patient and the treatment time based on the treatment planning information D3a obtained from the patient database.

Moreover, in the embodiment described as above, as one example, although a case that the available maximum diameter size of the electrode plate of the electrode part is within a range of "approximately 350 mm to 410 mm" being a size at the same level as the horizontal width of the human body of the average adult of Japanese (preferably, 400 mm) is described, in the present invention, when taking foreigners into consideration, it is also possible to employ a configuration capable of applying the electrode plate having a diameter size larger than that size (for example, the diameter size of about 410 mm to 500 mm). That is to say, the diameter size of the electrode plate of the maximum-sized electrode part can be within a range of "350 mm to 500 mm".

EXPLANATION OF REFERENCE NUMERALS 1 patient
1a affected part (cancer)
bed for thermotherapy
10A bed part
10B bed supporting part
11 bed part entering/leaving means (device for entering into/leaving from gantry)
12 bed part lifting/lowering means (pantographic arm type lifting/lowering device)
13 opening part for lower electrode pass
14 shutter
14a shutter lifting/lowering servomotor
14b shutter running servomotor
14C side cover
15 bed surface flatization means (slide table)
15a first table (opening part sliding connecting table)
15b second table (shutter interlock table)
15c third table
20 gantry
21 rotating ring (rotating drum)
21a roller (supporting roller)

22 expanding/contracting arm (arm for electrode mounting)
23 electrode pad tightly-adhering means
23a spherical joint
23b spring and eccentric cam (electrode angle fixing means)
24, 24A, 24B electrode part
24a electrode plate
24b electrode pad (pad for body surface temperature adjustment)
30 high frequency generation and control part
40 display for patient
50 operation controller for doctor

The invention claimed is:

1. A high frequency cancer thermotherapy apparatus configured to treat by generating a high frequency electric field between a pair of electrode parts sandwiching a patient, said electrode parts being opposite to each other and performing a dielectric heating with respect to an affected part of said patient, said high frequency cancer thermotherapy apparatus comprising:
a bed for thermotherapy that comprises a bed part for receiving said patient and a bed supporting part for liftably/lowerably and horizontally movably supporting said bed part;
a gantry that comprises a pair of expanding/contracting arms protruding from an inner peripheral surface of a rotating ring which can be controlled so as to pivot around said bed part and be opposite to each other, and on which said electrode parts are mounted;
a high frequency generation and control part configured to generate said high frequency electric field and perform a control with respect to each part of said high frequency cancer thermotherapy apparatus, and
an electrode pad adhering portion configured to make a surface of one of said electrode parts adhere to a body surface of said patent,
wherein said electrode pad adhering portion comprises:
a spherical joint configured to tiltably support said one of said electrode parts, said spherical joint being on a tip part of one of said expanding/contracting arms in an arbitrary direction,
an electrode angle fixing portion configured to fix a tilting angle of said one of said electrode parts, and
a pad surface which is made of soft material;
wherein a maximum-sized electrode part which can be mounted on said gantry is an electrode part comprising an electrode plate having a diameter size exceeding 300 mm and a pad attached on said electrode plate,
wherein said bed part comprises:
an opening part having a size such that said maximum-sized electrode part can pass from a vertical direction,
a shutter configured to open/close said opening part, and
slide tables for flatizing a level difference in a bed surface of said bed part which occurs in a state of closing said opening part by said shutter, and
wherein said slide tables comprise a first division table having a length in a longitudinal direction of said bed part that is longer than a length of said shutter, and a second division table having a length in said longitudinal direction of said bed part that is the same as said length of said shutter, and said slide tables are configured such that:
in a case of a first treatment aspect that treats by a vertical direction's high frequency from said electrode parts, said second division table is united with said shutter and housed in a lower part of said bed part in a state in which said patient is received on said bed part, and
in a case of a second treatment aspect that treats by a horizontal direction's high frequency from said electrode parts, said first division table is installed across both sides of said opening part in said longitudinal direction of said bed part, and concurrently, said shutter is configured to lower and close said opening part by a predetermined distance so as to avoid interference of a part of one of said electrode parts with parts of both sides of said bed part in a width direction.

2. A high frequency cancer thermotherapy apparatus configured to treat by generating a high frequency electric field between a pair of electrode parts sandwiching a patient, said electrode parts being opposite to each other and performing a dielectric heating with respect to an affected part of said patient, said high frequency cancer thermotherapy apparatus comprising:
a bed for thermotherapy that comprises a bed part for receiving said patient and a bed supporting part for liftably/lowerably and horizontally movably supporting said bed part;
a gantry that comprises a pair of expanding/contracting arms protruding from an inner peripheral surface of a rotating ring which can be controlled so as to pivot around said bed part and be opposite to each other, and on which said electrode parts are mounted;
a high frequency generation and control part configured to generate said high frequency electric field and perform a control with respect to each part of said high frequency cancer thermotherapy apparatus, and
an electrode pad adhering portion configured to make a surface of one of said electrode parts adhere to a body surface of said patent,
wherein said electrode pad adhering portion comprises:
a spherical joint configured to tiltably support said one of said electrode parts, said spherical joint being on a tip part of one of said expanding/contracting arms in an arbitrary direction,
an electrode angle fixing portion configured to fix a tilting angle of said one of said electrode parts, and
a pad surface which is made of soft material;
wherein a maximum-sized electrode part which can be mounted on said gantry is an electrode part comprising an electrode plate having a diameter size exceeding 300 mm and a pad attached on said electrode plate,
wherein said bed part comprises:
an opening part having a size such that said maximum-sized electrode part can pass from a vertical direction,
a shutter configured to open/close said opening part, and
slide tables for flatizing a level difference in a bed surface of said bed part which occurs in a state of closing said opening part by said shutter,
wherein said diameter size is the same as a horizontal width of a human body of an average adult, and
wherein said slide tables comprise a first division table having a length in a longitudinal direction of said bed part that is longer than a length of said shutter, and a second division table having a length in said longitudinal direction of said bed part that is the same as said length of said shutter, and said slide tables are configured such that:
in a case of a first treatment aspect that treats by a vertical direction's high frequency from said electrode parts, said second division table is united with said shutter and housed in a lower part of said bed part in a state in which said patient is received on said bed part, and
in a case of a second treatment aspect that treats by a horizontal direction's high frequency from said electrode parts, said first division table is installed across both sides of said opening part in said longitudinal direction of said bed part, and concurrently, said shutter is configured to lower and close said opening part by a predetermined distance so as to avoid interference of a part of one of said electrode parts with parts of both sides of said bed part in a width direction.

3. A high frequency cancer thermotherapy apparatus configured to treat by generating a high frequency electric field between a pair of electrode parts sandwiching a patient, said electrode parts being opposite to each other and performing a dielectric heating with respect to an affected part of said patient, said high frequency cancer thermotherapy apparatus comprising:

a bed for thermotherapy that comprises a bed part for receiving said patient and a bed supporting part for liftably/lowerably and horizontally movably supporting said bed part;

a gantry that comprises a pair of expanding/contracting arms protruding from an inner peripheral surface of a rotating ring which can be controlled so as to pivot around said bed part and be opposite to each other, and on which said electrode parts are mounted;

a high frequency generation and control part configured to generate said high frequency electric field and perform a control with respect to each part of said high frequency cancer thermotherapy apparatus, and an electrode pad adhering portion configured to make a surface of one of said electrode parts adhere to a body surface of said patent, wherein said electrode pad adhering portion comprises:

a spherical joint configured to tiltably support said one of said electrode parts, said spherical joint being on a tip part of one of said expanding/contracting arms in an arbitrary direction, an electrode angle fixing portion configured to fix a tilting angle of said one of said electrode parts, and a pad surface which is made of soft material;

wherein a maximum-sized electrode part which can be mounted on said gantry is an electrode part comprising an electrode plate having a diameter size exceeding 300 mm and a pad attached on said electrode plate, wherein said bed part comprises:

an opening part having a size such that said maximum-sized electrode part can pass from a vertical direction, a shutter configured to open/close said opening part, and slide tables for flatizing a level difference in a bed surface of said bed part which occurs in a state of closing said opening part by said shutter, wherein a pad of each of said electrode parts is a pad capable of switching cold water and warm water that flow within said pad and said high frequency cancer thermotherapy apparatus further comprises:

a temperature adjusting portion configured to adjust a temperature of said pad of each of said electrode parts by separately performing temperature control of said cold water and said warm water for said pad of each of said electrode parts;

a unit configured to monitor flow rates of said cold water and said warm water; and a unit configured to monitor abnormality in a pressing force of said pad of each of said electrode parts against a body surface of said patient, wherein said temperature adjusting portion is configured to preliminarily warm a temperature of said pad of each of said electrode parts by said warm water before bringing said pad of each of said electrode parts into contact with said body surface of said patient so that said temperature of said pad of each of said electrode parts is within a normal body temperature range of a body temperature of said patient, and wherein said temperature adjusting portion is further configured to switch from said warm water to said cold water so as to lower said temperature of said pad of each of said electrode parts in accordance with operations after bringing said pad of each of said electrode parts into contact with said body surface of said patient.

4. A high frequency cancer thermotherapy apparatus configured to treat by generating a high frequency electric field between a pair of electrode parts sandwiching a patient, said electrode parts being opposite to each other and performing a dielectric heating with respect to an affected part of said patient, said high frequency cancer thermotherapy apparatus comprising:

a bed for thermotherapy that comprises a bed part for receiving said patient and a bed supporting part for liftably/lowerably and horizontally movably supporting said bed part;

a gantry that comprises a pair of expanding/contracting arms protruding from an inner peripheral surface of a rotating ring which can be controlled so as to pivot around said bed part and be opposite to each other, and on which said electrode parts are mounted;

a high frequency generation and control part configured to generate said high frequency electric field and perform a control with respect to each part of said high frequency cancer thermotherapy apparatus, and an electrode pad adhering portion configured to make a surface of one of said electrode parts adhere to a body surface of said patent, wherein said electrode pad adhering portion comprises:

a spherical joint configured to tiltably support said one of said electrode parts, said spherical joint being on a tip part of one of said expanding/contracting arms in an arbitrary direction, an electrode angle fixing portion configured to fix a tilting angle of said one of said electrode parts, and a pad surface which is made of soft material;

wherein a maximum-sized electrode part which can be mounted on said gantry is an electrode part comprising an electrode plate having a diameter size exceeding 300 mm and a pad attached on said electrode plate, wherein said bed part comprises:

an opening part having a size such that said maximum-sized electrode part can pass from a vertical direction, a shutter configured to open/close said opening part, and slide tables for flatizing a level difference in a bed surface of said bed part which occurs in a state of closing said opening part by said shutter, wherein said diameter size is the same as a horizontal width of a human body of an average adult, wherein a pad of each of said electrode parts is a pad capable of switching cold water and warm water that flow within said pad and said high frequency cancer thermotherapy apparatus further comprises:

a temperature adjusting portion configured to adjust a temperature of said pad of each of said electrode parts by separately performing temperature control of said cold water and said warm water for said pad of each of said electrode parts;

a unit configured to monitor flow rates of said cold water and said warm water; and a unit configured to monitor abnormality in a pressing force of said pad of each of said electrode parts against a body surface of said patient, wherein said temperature adjusting portion is configured to preliminarily warm a temperature of said pad of each of said electrode parts by said warm water before bringing said pad of each of said electrode parts into contact with said body surface of said patient so that said temperature of said pad of each of said electrode parts is within a normal body temperature range of a body temperature of said patient, and wherein said temperature adjusting portion is further configured to switch from said warm water to said cold water so as to lower said temperature of said pad of each of said electrode parts in accordance with operations after bringing said pad of each of said electrode parts into contact with said body surface of said patient.

5. A high frequency cancer thermotherapy apparatus configured to treat by generating a high frequency electric field between a pair of electrode parts sandwiching a patient, said electrode parts being opposite to each other and performing a dielectric heating with respect to an affected part of said patient, said high frequency cancer thermotherapy apparatus comprising:

a bed for thermotherapy that comprises a bed part for receiving said patient and a bed supporting part for liftably/lowerably and horizontally movably supporting said bed part;

a gantry that comprises a pair of expanding/contracting arms protruding from an inner peripheral surface of a rotating ring which can be controlled so as to pivot around said bed part and be opposite to each other, and on which said electrode parts are mounted;

a high frequency generation and control part configured to generate said high frequency electric field and perform a control with respect to each part of said high frequency cancer thermotherapy apparatus, and an electrode pad adhering portion configured to make a surface of one of said electrode parts adhere to a body surface of said patent, wherein said electrode pad adhering portion comprises:

a spherical joint configured to tiltably support said one of said electrode parts, said spherical joint being on a tip part of one of said expanding/contracting arms in an arbitrary direction, an electrode angle fixing portion configured to fix a tilting angle of said one of said electrode parts, and a pad surface which is made of soft material;

wherein a maximum-sized electrode part which can be mounted on said gantry is an electrode part comprising an electrode plate having a diameter size exceeding 300 mm and a pad attached on said electrode plate, wherein said bed part comprises:

an opening part having a size such that said maximum-sized electrode part can pass from a vertical direction, a shutter configured to open/close said opening part, and slide tables for flatizing a level difference in a bed surface of said bed part which occurs in a state of closing said opening part by said shutter, wherein said high frequency generation and control part is configured to control a supply of high frequency energy to said electrode plate based on a measured temperature having an error obtained by removing noise of detection data of a temperature sensor for detecting a temperature of said affected part during a first treatment of said patient so that said temperature of said affected part enters a predetermined temperature range and said high frequency generation and control part is further configured to concurrently record measurement data of a living body impedance of said patient, and wherein said high frequency generation and control part comprises a heating control portion configured to control said supply of high frequency energy to said electrode plate based on said measurement data of said living body impedance of said patient without detecting said temperature of said affected part again during a second treatment of said patient so that said temperature of said affected part enters said predetermined temperature range.

\* \* \* \* \*